US012577264B2

(12) United States Patent
Fujimoto

(10) Patent No.: US 12,577,264 B2
(45) **Date of Patent: *Mar. 17, 2026**

(54) BORATE COMPOUND-CONTAINING COMPOSITION

(71) Applicant: AGC INC., Tokyo (JP)

(72) Inventor: Takuya Fujimoto, Tokyo (JP)

(73) Assignee: AGC INC., Tokyo (JP)

( * ) Notice: Subject to any disclaimer, the term of this patent is extended or adjusted under 35 U.S.C. 154(b) by 789 days.

This patent is subject to a terminal disclaimer.

(21) Appl. No.: 17/941,067

(22) Filed: Sep. 9, 2022

(65) Prior Publication Data

US 2023/0021628 A1 Jan. 26, 2023

Related U.S. Application Data

(63) Continuation of application No. PCT/JP2021/009165, filed on Mar. 9, 2021.

(30) Foreign Application Priority Data

Mar. 12, 2020 (JP) ................................ 2020-043246
Dec. 17, 2020 (JP) ................................ 2020-209070

(51) Int. Cl.

*C07F 5/02* (2006.01)
*B01J 31/02* (2006.01)
*C07D 213/16* (2006.01)
*C07D 235/04* (2006.01)

(52) U.S. Cl.

CPC ................ *C07F 5/02* (2013.01); *B01J 31/02* (2013.01); *C07D 213/16* (2013.01); *C07D 235/04* (2013.01)

(58) Field of Classification Search

CPC .......... C07F 5/02; B01J 31/02; C07D 213/16; C07D 235/04

See application file for complete search history.

(56) References Cited

U.S. PATENT DOCUMENTS

| | | | |
|---|---|---|---|
| 5,919,983 A | 7/1999 | Rosen et al. | |
| 6,121,185 A | 9/2000 | Rosen et al. | |
| 7,101,940 B2 | 9/2006 | Schottek et al. | |
| 8,969,482 B2 | 3/2015 | Stewart | |
| 9,611,280 B2 | 4/2017 | Takaishi et al. | |
| 11,041,031 B2 | 6/2021 | Faler et al. | |
| 11,117,908 B2 | 9/2021 | Faler et al. | |
| 11,414,436 B2 | 8/2022 | Faler et al. | |
| 2001/0014739 A1 | 8/2001 | Mitsui et al. | |
| 2003/0013913 A1 | 1/2003 | Schottek et al. | |
| 2007/0197831 A1 | 8/2007 | Lee et al. | |
| 2013/0085232 A1 | 4/2013 | Stewart | |
| 2016/0108062 A1 | 4/2016 | Takaishi et al. | |
| 2019/0330139 A1 | 10/2019 | Faler et al. | |
| 2019/0330246 A1 | 10/2019 | Faler et al. | |
| 2019/0330392 A1 | 10/2019 | Faler et al. | |
| 2020/0339517 A1* | 10/2020 | Faler et al. | C07D 235/06 |

FOREIGN PATENT DOCUMENTS

| | | |
|---|---|---|
| EP | 1 250 363 B1 | 8/2006 |
| EP | 2 998 306 A1 | 3/2016 |
| JP | 10-310587 A | 11/1998 |

(Continued)

OTHER PUBLICATIONS

JP 2019059795 A (Kaneko, IDS reference; Original Document and English language machine translation) (Year: 2019).*
WO 2019/098703 A1 (Kim et al.; Original Document and English language machine translation) (Year: 2019).*
Xu et al., "Room temperature ionic liquids based on cationic porphyrin derivatives and tetrakis(pentafluorophenyl)borate anion", Journal of Porphyrins and Phthalocyanines, 2011, vol. 15, pp. 560-574.

*Primary Examiner* — Amy C Bonaparte
*Assistant Examiner* — Derek Rhoades
(74) *Attorney, Agent, or Firm* — Oblon, McClelland, Maier & Neustadt, L.L.P.

(57) ABSTRACT

A borate compound-containing composition soluble in hydrocarbon solvents. A composition containing base A, or a compound having a total carbon number of not less than 8 and represented by the formula (5):

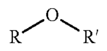

(5)

wherein R and R' are each independently an optionally substituted $C_{1-30}$ alkyl group, an optionally substituted $C_{3-15}$ cycloalkyl group, or an optionally substituted $C_{6-14}$ aryl group; and a borate compound represented by the following formula (1):

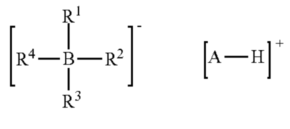

(1)

wherein $R^1$, $R^2$, $R^3$ and $R^4$ are each independently a $C_{6-14}$ aryl group substituted by one or more fluorine atoms or fluoro $C_{1-4}$ alkyl groups; and $[A-H]^+$ is a base A-derived cation. A method for producing a polymer, by polymerizing at least one kind of monomer selected from the group consisting of olefins and dienes by using the composition A as a cocatalyst.

18 Claims, No Drawings

(56) References Cited

FOREIGN PATENT DOCUMENTS

| | | | | |
|---|---|---|---|---|
| JP | 2000-507157 A | | 6/2000 | |
| JP | 2007-530673 A | | 11/2007 | |
| JP | 2018-104335 A | | 7/2018 | |
| JP | 2019-59795 A | | 4/2019 | |
| KR | 10-1367364 B1 | | 2/2014 | |
| WO | WO 2013/048848 A2 | | 4/2013 | |
| WO | WO 2019098703 A1 | * | 5/2019 | ................ C08F 2/38 |
| WO | WO 2019/210026 A1 | | 10/2019 | |

* cited by examiner

BORATE COMPOUND-CONTAINING COMPOSITION

CROSS REFERENCE TO RELATED APPLICATIONS

This application is a continuation application of PCT/JP2021/009165, filed on Mar. 9, 2021, and claims priority to Japanese Patent Application No. 2020-043246, filed on Mar. 12, 2020, and Japanese Patent Application No. 2020-209070, filed on Dec. 17, 2020, the entire contents of which are incorporated herein by reference.

TECHNICAL FIELD

The present invention relates to a composition containing a borate compound and a base, and useful as a cocatalyst for polymerization of olefins or dienes, and a production method thereof.

BACKGROUND ART

Many reports have been conventionally made on the use of metallocene compound and non-metallocene type metal complex catalysts such as diimine complex, phenoxy complex, and the like as catalysts for the polymerization of olefins and dienes. In many of these catalytic systems using metal complex catalysts, methylaluminoxane and tetrakis(pentafluorophenyl)borate compounds are used as cocatalysts for stabilizing active species. Tetrakis(pentafluorophenyl)borate compounds are widely used as cocatalysts in solution polymerization systems since they are superior to methylaluminoxane in thermal stability, and the stoichiometric ratio used for metal complexes is lower than that of methylaluminoxane.

In addition, as a solvent used for polymerization of olefins and dienes by a metal complex catalyst, a non-polar hydrocarbon solvent is used. In particular, from the aspects of odor and toxicity, switching to aliphatic hydrocarbon solvents such as hexane and the like from aromatic hydrocarbon solvents such as toluene and the like is progressing.

However, it is known that general tetrakis(pentafluorophenyl)borate compounds are hardly soluble in aromatic hydrocarbon solvents such as toluene and the like, and that even if dissolved, they are separated to form two liquid-liquid phases of a concentrated phase in which the borate compound is dissolved and a dilute phase in which it is not dissolved (Patent document 1).

In addition, since general tetrakis(pentafluorophenyl)borate compounds are hardly soluble in aliphatic hydrocarbon solvents such as hexane, heptane, and the like, a tetrakis(pentafluorophenyl)borate compound soluble in aliphatic hydrocarbon solvents is desired and has been proposed (Patent document 2). Di(octadecyl)methylammonium tetrakis(pentafluorophenyl)borate and bis(hydrogenated tallow)methylammonium tetrakis(pentafluorophenyl)borate described in Patent document 2 are useful as compounds easily soluble in hydrocarbon solvents.

However, in the production method described in Patent document 2, lithium tetrakis(pentafluorophenyl)borate and hydrochloride of dialkylmethylamine prepared separately are reacted for preparation. With regard to this method, it is feared that lithium tetrakis(pentafluorophenyl)borate, which is a hardly water-soluble starting material, or hydrochloride of long chain aliphatic amine remains in the resultant product to be a catalyst poison, which prevents exhibition of sufficient activity when used as a cocatalyst for polymerization. In fact, in Example 2 of Patent document 2, since diethyl ether remains in the resultant product, it is presumed that a diethyl ether complex of hardly water-soluble lithium tetrakis(pentafluorophenyl)borate remains.

Patent document 3 discloses a production method of an ammonium tetrakis(pentafluorophenyl)borate derivative by mixing an alkali metal salt of tetrakis(pentafluorophenyl)borate with an amine, and then treating the mixture with a protic acid. However, even in this method, it is feared that an ether complex of an alkali metal salt of tetrakis(pentafluorophenyl)borate or a protic acid salt of long chain aliphatic amine remains in the resultant product and acts as a catalyst poison.

Patent document 4 discloses a composition containing a trialkyl ammonium tetrakis(pentafluorophenyl)borate compound and an amine compound, and a production method thereof, and discloses that the composition is soluble in hydrocarbon solvents. However, trialkylamine which is the amine compound described in Patent document 4 has high basicity and also has nucleophilic property. Thus, it is feared that it becomes a catalyst poison in the polymerization reaction of olefins or diener.

CITATION LIST

Patent Document

[Patent Document 1]
JP-A-2018-104335
[Patent Document 2]
Japanese Translation of PCT Application Publication No. 2000-507157
[Patent Document 3]
Japanese Translation of PCT Application Publication No. 2007-530673
[Patent Document 4]
JP-A-2019-59795

SUMMARY OF INVENTION

Problems to be Solved by the Invention

In view of those conventional techniques, the present invention aims to provide a borate compound-containing composition, which is soluble in hydrocarbon solvents, particularly aliphatic hydrocarbon solvents, and does not become a catalyst poison for the polymerization reaction of olefin and diene, and an industrial production method thereof.

Means of Solving the Problems

The present inventors have conducted intensive studies and found for the first time that a composition containing (I) base A or a compound having a total carbon number of not less than 8 and represented by the following formula (5):

(5)

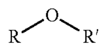

wherein R and R' are each independently an optionally substituted $C_{1-30}$ alkyl group, an optionally substituted $C_{3-15}$ cycloalkyl group, or an optionally substituted $C_{6-14}$ aryl group, and (II) a compound represented by the following formula (1):

(1)

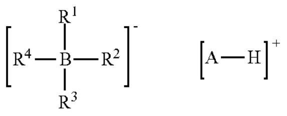

wherein $R^1$, $R^2$, $R^3$ and $R^4$ are each independently a $C_{6-14}$ aryl group substituted by one or more fluorine atoms or fluoro $C_{1-4}$ alkyl groups, and $[A-H]^+$ is a base A-derived cation, wherein the aforementioned base A is (i) a nitrogen-containing aromatic heterocyclic compound having a total carbon number of not less than 25 and substituted by the same or different, two or more $C_{1-30}$ alkyl groups or $C_{1-30}$ alkoxy groups, or (ii) an aromatic amine compound having a total carbon number of not less than 25 and represented by the following formula (2):

(2)

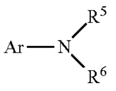

wherein Ar is an optionally substituted $C_{6-14}$ aryl group, and $R^5$ and $R^6$ are each independently an optionally substituted $C_{1-30}$ alkyl group (hereinafter to be also referred to as "the composition of the present invention") is soluble in hydrocarbon solvents, particularly aliphatic hydrocarbon solvents, does not allow generation of a compound to be a catalyst poison for the polymerization reaction of olefin and diene, and is useful as a cocatalyst, and completed the present invention.

Accordingly, the present invention provides the following.

[1] A composition comprising (I) base A or a compound having a total carbon number of not less than 8 and represented by the following formula (5):

(5)

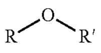

wherein R and R' are each independently an optionally substituted $C_{1-30}$ alkyl group, an optionally substituted $C_{3-15}$ cycloalkyl group, or an optionally substituted $C_{6-14}$ aryl group, and (II) a compound represented by the following formula (1):

(1)

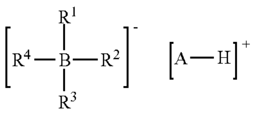

wherein $R^1$, $R^2$, $R^3$ and $R^4$ are each independently a $C_{6-14}$ aryl group substituted by one or more fluorine atoms or fluoro $C_{1-4}$ alkyl groups, and $[A-H]^+$ is a base A-derived cation, wherein the aforementioned base A is (i) a nitrogen-containing aromatic heterocyclic compound having a total carbon number of not less than 25 and substituted by the same or different, two or more $C_{1-30}$ alkyl groups or $C_{1-30}$ alkoxy groups, or (ii) an aromatic amine compound having a total carbon number of not less than 25 and represented by the following formula (2):

(2)

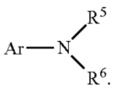

wherein Ar is an optionally substituted $C_{6-14}$ aryl group, and $R^5$ and $R^6$ are each independently an optionally substituted $C_{1-30}$ alkyl group.

[2] A composition comprising base A and a compound represented by the following formula (1):

(1)

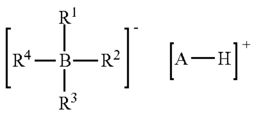

wherein $R^1$, $R^2$, $R^3$ and $R^4$ are each independently a $C_{6-14}$ aryl group substituted by one or more fluorine atoms or fluoro $C_{1-4}$ alkyl groups, and $[A-H]^+$ is a base A-derived cation, wherein the aforementioned base A is (i) a nitrogen-containing aromatic heterocyclic compound having a total carbon number of not less than 25 and substituted by the same or different, two or more $C_{1-30}$ alkyl groups or $C_{1-30}$ alkoxy groups, or (ii) an aromatic amine compound having a total carbon number of not less than 25 and represented by the following formula (2):

(2)

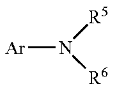

wherein Ar is an optionally substituted $C_{6-14}$ aryl group, and $R^5$ and $R^6$ are each independently an optionally substituted $C_{1-30}$ alkyl group.

[2'] The composition of the aforementioned [1], wherein the component (I) is base A.

[3] The composition of the aforementioned [1], wherein the component (I) is a compound represented by the aforementioned formula (5).

[4] The composition of any of the aforementioned [1] to [3], wherein $R^1$, $R^2$, $R^3$ and $R^4$ are each independently a phenyl group, a 1-naphthyl group, a 2-naphthyl group, a 2-biphenylyl group, a 3-biphenylyl group, a 4-biphenylyl group, a 1-anthryl group, a 2-anthryl group, a 9-anthryl group, a 9-phenanthryl group, or a 3-phenanthryl group, each of which is substituted by one or more fluorine atoms or trifluoromethyl groups.

[5] The composition of any of the aforementioned [1] to [3], wherein all of $R^1$, $R^2$, $R^3$ and $R^4$ are pentafluorophenyl groups, 2,2',3,3',4',5,5',6,6'-nonafluoro-4-(1,1'-biphenylyl) groups, 2,3,4,5,6,7,8-heptafluoro-1-naphthyl groups, or 1,3,4,5,6,7,8-heptafluoro-2-naphthyl groups.

[6] The composition of any of the aforementioned [1], [2], [2'], [4], and [5], wherein the base A is a 5- or 6-membered monocyclic nitrogen-containing aromatic heterocyclic compound having a total carbon number of not less than 35 and substituted by the same or different two $C_{9-30}$ alkyl groups or $C_{9-30}$ alkoxy groups.

[7] The composition of the aforementioned [6], wherein the 5- or 6-membered monocyclic nitrogen-containing aromatic heterocyclic compound is pyridine or imidazole.

[8] The composition of any of [1], [2], [2'], [4], and [5], wherein the base A is a bicyclic nitrogen-containing aromatic heterocyclic compound having a total carbon number of not less than 25 and substituted by the same or different two $C_{9-30}$ alkyl groups or $C_{9-30}$ alkoxy groups.

[9] The composition of the aforementioned [8], wherein the bicyclic nitrogen-containing aromatic heterocyclic compound is benzimidazole.

[10] The composition of any of the aforementioned [1], [2], [2'], [4], and [5], wherein the base A is an aromatic amine compound having a total carbon number of not less than 25 and represented by the aforementioned formula (2), Ar is a phenyl group optionally substituted by substituent(s) selected from the group consisting of a halogen atom, a $C_{1-30}$ alkyl group, a $C_{1-30}$ alkoxy group, and a halo $C_{1-6}$ alkyl group, and $R^5$ and $R^6$ are each independently a $C_{1-30}$ alkyl group.

[11] The composition of any of the aforementioned [1], [2], [2'] and [4]-[10], wherein a content of the aforementioned base A with respect to 1 mol of the compound represented by the aforementioned formula (1) is within the range of 0.01 to 10 mol.

[12] The composition of any of the aforementioned [1] and [3] to [5], wherein the R and R' are each independently a $C_{1-30}$ alkyl group, and the total carbon number of the R and R' is not less than 8.

[13] The composition of any of the aforementioned [1] and [3] to [5], wherein the R and R' are each independently a $C_{1-30}$ alkyl group, and the total carbon number of the R and R' is not less than 16.

[14] The composition of any of the aforementioned [1], [3] to [5], [12], and [13], wherein a content of the compound represented by the aforementioned formula (5) with respect to 1 mol of the compound represented by the aforementioned formula (1) is within the range of 0.1-10 mol.

[15] A cocatalyst for polymerization of at least one kind of monomer selected from the group consisting of an olefin and a diene, consisting of the composition of any of the aforementioned [1] to [14].

[16] A method for producing the composition of any of the aforementioned [1], [2], [2'] and [4] to [11], comprising a step of reacting a compound represented by the formula (3):

(3)

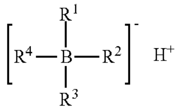

wherein $R^1$, $R^2$, $R^3$ and $R^4$ are each independently a $C_{6-14}$ aryl group substituted by one or more fluorine atoms or fluoro $C_{1-4}$ alkyl groups, and the aforementioned base A, wherein the base A is used in an amount exceeding 1 mol per 1 mol of the compound represented by the aforementioned formula (3).

[17] The production method of the aforementioned [16], wherein the amount of the aforementioned base A is within the range of 1.01 to 3 mol with respect to 1 mol of the compound represented by the formula (3).

[18] A method for producing the composition of any of the aforementioned [1], [2], [2'] and [4] to [11], comprising a step of reacting a compound represented by the formula (4):

(4)

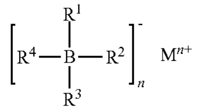

wherein $R^1$, $R^2$, $R^3$ and $R^4$ are each independently a $C_{6-14}$ aryl group substituted by one or more fluorine atoms or fluoro $C_{1-4}$ alkyl groups, M is an alkali metal or an alkaline earth metal, and n is 1 or 2, the aforementioned base A, and protonic acid, wherein the base A is used in an amount exceeding 1 mol per 1 mol of the compound represented by the aforementioned formula (4).

[19] A method for producing the composition of any of the aforementioned [1], [3] to [5], and [12] to [14], comprising a step of reacting a compound represented by the formula (4):

(4)

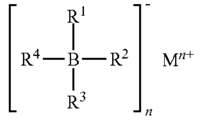

wherein $R^1$, $R^2$, $R^3$ and $R^4$ are each independently a $C_{6-14}$ aryl group substituted by one or more fluorine atoms or fluoro $C_{1-4}$ alkyl groups, M is an alkali metal or an alkaline earth metal, and n is 1 or 2, and 1 mol of the aforementioned base A per 1 mol of the compound represented by the aforementioned formula (4) and protonic acid, and thereafter, a step of adding not less than 0.1 mol of a compound having a total carbon number of not less than 8 and represented by the formula (5):

(5)

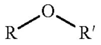

wherein R and R' are each independently an optionally substituted $C_{1-30}$ alkyl group, an optionally substituted $C_{3-15}$ cycloalkyl group, or an optionally substituted $C_{6-14}$ aryl group, per 1 mol of the compound represented by the aforementioned formula (4).

[20] A method for producing a polymer, comprising polymerizing at least one kind of monomer selected from the group consisting of olefins and dienes by using the composition of any of the aforementioned [1] to [14] as a cocatalyst.

Effect of the Invention

According to the present invention, a composition containing the aforementioned borate compound which is soluble in hydrocarbon solvents, particularly aliphatic hydrocarbon solvents, and useful as a cocatalyst for polymerization of olefins or dienes, and a production method thereof can be provided.

DESCRIPTION OF EMBODIMENTS

The definitions of the terms and respective symbols used in the present specification are explained below.

In the present specification, the “halogen atom” means a fluorine atom, a chlorine atom, a bromine atom, or an iodine atom.

In the present specification, the “alkyl (group)” means a linear or branched chain alkyl group having a carbon number of not less than 1.

In the present specification, the “$C_{1-30}$ alkyl (group)” means a linear or branched chain alkyl group having a carbon number of 1 to 30. Examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl, dodecyl, tridecyl, tetradecyl, hexadecyl, octadecyl, nonadecyl, eicosyl, docosyl, tricosyl, tetracosyl, pentacosyl, hexacosyl, heptacosyl, octacosyl, nonacosyl, triacontyl, and the like.

In the present specification, the “$C_{9-30}$ alkyl (group)” means a linear or branched chain alkyl group having a carbon number of 9 to 30. Examples thereof include nonyl, decyl, undecyl, dodecyl, tridecyl, tetradecyl, hexadecyl, octadecyl, nonadecyl, eicosyl, docosyl, tricosyl, tetracosyl, pentacosyl, hexacosyl, heptacosyl, octacosyl, nonacosyl, triacontyl, and the like.

In the present specification, the “$C_{1-6}$ alkyl (group)” means a linear or branched chain alkyl group having a carbon number of 1 to 6. Examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, and the like. Among them, $C_{1-4}$ alkyl group is preferred.

In the present specification, the “halo $C_{1-6}$ alkyl (group)” means the aforementioned “$C_{1-6}$ alkyl” group in which one or more hydrogen atoms are substituted by halogen atom(s). Specific examples thereof include difluoromethyl, trifluoromethyl, 2-chloroethyl, 2-bromoethyl, 2-iodoethyl, 2-fluoroethyl, 2,2-difluoroethyl, 2,2,2-trifluoroethyl, pentafluoroethyl, 2,2,3,3-tetrafluoropropyl, 3,3,3-trifluoropropyl, 4,4,4-trifluorobutyl, 5,5,5-trifluoropentyl, 6,6,6-trifluorohexyl, and the like. Among them, “halo $C_{1-4}$ alkyl” is preferred.

In the present specification, the “fluoro $C_{1-6}$ alkyl (group)” means the aforementioned “halo $C_{1-6}$ alkyl” group in which the halogen atom is a fluorine atom. Specific examples thereof include difluoromethyl, trifluoromethyl, 2-fluoroethyl, 2,2-difluoroethyl, 2,2,2-trifluoroethyl, pentafluoroethyl, 2,2,3,3-tetrafluoropropyl, 3,3,3-trifluoropropyl, 4,4,4-trifluorobutyl, 5,5,5-trifluoropentyl, 6,6,6-trifluorohexyl, and the like. Among them, “fluoro $C_{1-4}$ alkyl (groups)” such as difluoromethyl, trifluoromethyl, 2-fluoroethyl, 2,2-difluoroethyl, 2,2,2-trifluoroethyl, pentafluoroethyl, 2,2,3,3-tetrafluoropropyl, 3,3,3-trifluoropropyl, 4,4,4-trifluorobutyl, 5,5,5-trifluoropentyl, 6,6,6-trifluorohexyl and the like are preferred, and difluoromethyl, trifluoromethyl, 2,2,2-trifluoroethyl, pentafluoroethyl, and pentafluoroethyl are more preferred, and trifluoromethyl is particularly preferred.

In the present specification, the “cycloalkyl (group)” means a cyclic alkyl group. Unless the carbon number range is particularly limited, it is preferably a $C_{3-8}$ cycloalkyl group.

In the present specification, the “$C_{3-8}$ cycloalkyl (group)” means a cyclic alkyl group having a carbon number of 3 to 8. Examples thereof include cyclopropyl, cyclobutyl, cyclopentyl, cyclohexyl, cycloheptyl, cyclooctyl, and the like. Among them, a $C_{3-6}$ cycloalkyl group is preferred.

In the present specification, the “alkoxy (group)” means a group in which a linear or branched chain alkyl group is bonded to an oxygen atom.

In the present specification, the “$C_{1-30}$ alkoxy (group)” means a linear or branched chain alkoxy group having a carbon number of 1 to 30. Examples thereof include methoxy, ethoxy, propoxy, isopropoxy, butoxy, isobutoxy, sec-butoxy, tert-butoxy, pentyloxy, isopentyloxy, neopentyloxy, hexyloxy, isohexyloxy, 1,1-dimethylbutoxy, 2,2-dimethylbutoxy, 3,3-dimethylbutoxy, 2-ethylbutoxy, heptyloxy, octyloxy, nonyloxy, decyloxy, undecyloxy, dodecyloxy, tridecyloxy, tetradecyloxy, hexadecyloxy, octadecyloxy, nonadecyloxy, eicosyloxy, docosyloxy, tricosyloxy, tetracosyloxy, pentacosyloxy, hexacosyloxy, heptacosyloxy, octacosyloxy, nonacosyloxy, triacontyloxy, and the like.

In the present specification, “$C_{9-30}$ alkoxy (group)” means a linear or branched chain alkoxy group having a carbon number of 9 to 30. Examples thereof include nonyloxy, decyloxy, undecyloxy, dodecyloxy, tridecyloxy, tetradecyloxy, hexadecyloxy, octadecyloxy, nonadecyloxy, eicosyloxy, docosyloxy, tricosyloxy, tetracosyloxy, pentacosyloxy, hexacosyloxy, heptacosyloxy, octacosyloxy, nonacosyloxy, triacontyloxy, and the like.

In the present specification, the “$C_{1-6}$ alkoxy (group)” means a linear or branched chain alkoxy group having a carbon number of 1 to 6. Examples thereof include methoxy, ethoxy, propoxy, isopropoxy, butoxy, isobutoxy, sec-butoxy, tert-butoxy, pentyloxy, isopentyloxy, neopentyloxy, hexyloxy, and the like. Among them, a $C_{1-4}$ alkoxy group is preferred.

In the present specification, the “halo $C_{1-6}$ alkoxy (group)” means the aforementioned “$C_{1-6}$ alkoxy” group in which one or more hydrogen atoms are substituted by halogen atom(s). Specific examples thereof include difluoromethoxy, trifluoromethoxy, 2-chloroethoxy, 2-bromoethoxy, 2-iodoethoxy, 2-fluoroethoxy, 2,2-difluoroethoxy, 2,2,2-trifluoroethoxy, pentafluoroethoxy, 2,2,3,3,3- pentafluoropropoxy, 2,2,3,3-tetrafluoropropoxy, 3,3,3-trifluoropropoxy, 4,4,4-trifluorobutoxy, 5,5,5-trifluoropentyloxy, 6,6,6-trifluorohexyloxy, and the like. Among them, "halo $C_{1-4}$ alkoxy" is preferred.

In the present specification, the "fluoro $C_{1-6}$ alkoxy (group)" means the aforementioned "halo $C_{1-6}$ alkoxy" group in which the halogen atom is a fluorine atom. Specific examples thereof include difluoromethoxy, trifluoromethoxy, 2-fluoroethoxy, 2,2-difluoroethoxy, 2,2,2-trifluoroethoxy, pentafluoroethoxy, 2,2,3,3-tetrafluoropropoxy, 3,3,3-trifluoropropoxy, 4,4,4-trifluorobutoxy, 5,5,5-trifluoropentyloxy, 6,6,6-trifluorohexyloxy, and the like. Among them, "fluoro $C_{1-4}$ alkoxy (groups)" such as difluoromethoxy, trifluoromethoxy, 2,2,2-trifluoroethoxy, pentafluoroethoxy, 2,2,3,3,3-pentafluoropropoxy, 2,2,3,3-tetrafluoropropoxy, 3,3,3-trifluoropropoxy, 4,4,4-trifluorobutoxy, and the like are preferred; difluoromethoxy, trifluoromethoxy, 2,2,2-trifluoroethoxy, pentafluoroethoxy, and pentafluoroethoxy are more preferred; and trifluoromethoxy is are particularly preferred.

In the present specification, the "aryl (group)" mean a monocyclic or polycyclic (fused) hydrocarbon group showing aromaticity. Specific examples thereof include $C_{6-14}$ aryl groups such as phenyl, 1-naphthyl, 2-naphthyl, 2-biphenylyl, 3-biphenylyl, 4-biphenylyl, 1-anthryl, 2-anthryl, 9-anthryl, 3-phenanthryl, 9-phenanthryl, and the like. Among them, phenyl, 1-naphthyl, and 2-naphthyl are preferred.

In the present specification, the "nitrogen-containing aromatic heterocyclic compound" means a monocyclic or fused polycyclic aromatic heterocyclic compound containing, besides a carbon atom, 1 to 4 hetero atoms selected from a nitrogen atom, a sulfur atom, and an oxygen atom as ring-constituting atom(s), and containing at least one nitrogen atom as the ring-constituting atom.

Preferable examples of the "nitrogen-containing aromatic heterocyclic compound" include 5- or 6-membered monocyclic nitrogen-containing aromatic heterocyclic compounds such as pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine, and the like; 8-to 14-membered fused polycyclic (preferably bi- or tri-cyclic) nitrogen-containing aromatic heterocyclic compounds such as benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolotriazine, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine, and the like, and a 5- or 6-membered monocyclic nitrogen-containing aromatic heterocyclic compound and a bicyclic nitrogen-containing aromatic heterocyclic compound are preferred. As the 5- or 6-membered monocyclic nitrogen-containing aromatic heterocyclic compound, pyridine and imidazole are more preferred. As the bicyclic nitrogen-containing aromatic heterocyclic compound, benzimidazole is more preferred. Among them, pyridine and imidazole are particularly preferred.

In the present specification, the "optionally substituted" means unsubstituted or having one or more substituents. Unless otherwise particularly indicated, (1) a halogen atom, (2) a nitro group, (3) a cyano group, (4) a $C_{1-30}$ alkyl group, (5) a halo $C_{1-6}$ alkyl group, (6) a $C_{3-8}$ cycloalkyl group, (7) a $C_{1-30}$ alkoxy group, (8) a halo $C_{1-6}$ alkoxy group, (9) a $C_{6-14}$ aryl group, and the like can be mentioned as the "substituent". Among them, a halogen atom, a cyano group, a $C_{1-6}$ alkyl group, a halo $C_{1-6}$ alkyl group, a $C_{1-6}$ alkoxy group, a halo $C_{1-6}$ alkoxy group, and a phenyl group are preferred, and a halogen atom (e.g., fluorine atom), a $C_{1-6}$ alkyl group (e.g., methyl, ethyl), a $C_{1-6}$ alkoxy group (e.g., methoxy, ethoxy), and a halo $C_{1-6}$ alkyl group (e.g., trifluoromethyl) are more preferred. When plural substituents are present, respective substituents may be the same or different. The above-mentioned substituents may also be further substituted by one or more of a $C_{1-6}$ alkyl group, a $C_{1-6}$ alkoxy group, a halogen atom, a phenyl group, and the like.

In the present specification, the "hydrocarbon solvent" means solvents including aromatic hydrocarbon solvents and/or aliphatic hydrocarbon solvents. Among them, aliphatic hydrocarbon solvents are preferable from the aspects of odor and toxicity.

In the present specification, examples of the "aromatic hydrocarbon solvent" include benzene, toluene, xylene, and the like.

In the present specification, examples of the "aliphatic hydrocarbon solvent" include n-hexane, isohexane, n-heptane, n-octane, cyclohexane, methylcyclohexane, a mixed solvent thereof, and the like.

In the present specification, the "soluble in hydrocarbon solvent (or aliphatic hydrocarbon solvent)" means that the composition of the present invention is dissolved in a solution of a hydrocarbon solvent (or aliphatic hydrocarbon solvent) and the composition of the present invention at 25° C. at a concentration of not less than 5 wt % to form a transparent homogeneous solution. In addition, the "easily soluble in hydrocarbon solvent (or aliphatic hydrocarbon solvent)" means that the composition of the present invention is dissolved in a solution of a hydrocarbon solvent (or aliphatic hydrocarbon solvent) and the composition of the present invention at 25° C. at a concentration of not less than 20 wt % (preferably not less than 30 wt %) to form a transparent homogeneous solution.

(Composition of the Present Invention)

The composition of the present invention is explained below.

The composition of the present invention is a composition containing (I) base A or a compound having a total carbon number of not less than 8 and represented by the following formula (5):

(5)

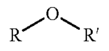

wherein R and R' are each independently an optionally substituted $C_{1-30}$ alkyl group, an optionally substituted $C_{3-15}$ cycloalkyl group, or an optionally substituted $C_{6-14}$ aryl group, and (II) a compound represented by the following formula (1):

(1)

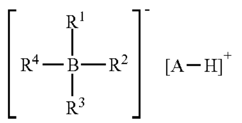

wherein $R^1$, $R^2$, $R^3$ and $R^4$ are each independently a $C_{6-14}$ aryl group substituted by one or more fluorine atoms or fluoro $C_{1-4}$ alkyl groups, and $[A-H]^+$ is a base A-derived cation, wherein the aforementioned base A is (i) a nitrogen-containing aromatic heterocyclic compound having a total carbon number of not less than 25 and substituted by the same or different, two or more $C_{1-30}$ alkyl groups or $C_{1-30}$ alkoxy groups, or (ii) an aromatic amine compound having a total carbon number of not less than 25 and represented by the following formula (2):

(2)

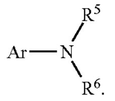

wherein Ar is an optionally substituted $C_{6-14}$ aryl group, and $R^5$ and $R^6$ are each independently an optionally substituted $C_{1-30}$ alkyl group.

A preferred embodiment of base A is explained below.

As the nitrogen-containing aromatic heterocyclic compound as (i) for base A, a 5- or 6-membered monocyclic nitrogen-containing aromatic heterocyclic compound (e.g., pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine, etc.) substituted by the same or different two $C_{9-30}$ alkyl groups or $C_{9-30}$ alkoxy groups is preferred, and pyridine or imidazole substituted by the same or different two $C_{14-30}$ alkyl groups or $C_{14-30}$ alkoxy groups is more preferred.

The nitrogen-containing aromatic heterocyclic compound preferably has a total carbon number of not less than 25, more preferably has a total carbon number of not less than 30, further preferably not less than 35.

Specific preferable examples of the nitrogen-containing aromatic heterocyclic compound as base A include 2,5-dinonadecylpyridine, 2,6-dinonadecylpyridine, 2-nonadecyl-5-octadecylpyridine, 2-nonadecyl-4-octadecyloxypyridine, 2-nonadecyl-6-octadecyloxypyridine, 4-nonadecyl-1-octadecylimidazole, 5-nonadecyl-1-octadecylimidazole, 2-nonadecyl-1-octadecylimidazole, and the like.

As another preferable nitrogen-containing aromatic heterocyclic compound as (i) for base A, a bicyclic nitrogen-containing aromatic heterocyclic compound (e.g., benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolotriazine, indole, isoindole, 1H-indazole, purine, isoquinoline, quinoline, phthalazine, naphthyridine, quinoxaline, quinazoline, cinnoline, etc.) substituted by the same or different two $C_{9-30}$ alkyl groups or $C_{9-30}$ alkoxy groups can be mentioned. Among them, benzimidazole substituted by the same or different two $C_{9-30}$ alkyl groups or $C_{9-30}$ alkoxy groups (further preferably, $C_{14-30}$ alkyl groups or $C_{14-30}$ alkoxy groups) is more preferred.

The nitrogen-containing aromatic heterocyclic compound preferably has a total carbon number of not less than 25, more preferably has a total carbon number of not less than 30, further preferably not less than 35.

Specific examples of another preferable nitrogen-containing aromatic heterocyclic compound as base A include 2,6-dinonadecylbenzimidazole, 1,2-dioctadecylbenzimidazole, 1,2-diheptadecylbenzimidazole, 2-heptadecyl-1-octadecylbenzimidazole, 1-heptadecyl-2-octadecylbenzimidazole, and the like.

As the aromatic amine compound represented by the formula (2) as (ii) for base A (hereinafter to be also referred to as "compound (2)"), Ar in the aforementioned formula (2) is preferably a $C_{6-14}$ aryl group optionally substituted by substituent(s) selected from the group consisting of a halogen atom, a cyano group, a $C_{1-30}$ alkyl group, a halo $C_{1-6}$alkyl group, a $C_{1-30}$ alkoxy group, and a halo $C_{1-6}$ alkoxy group, more a preferably phenyl group, a 1-naphthyl group, or a 2-naphthyl group (particularly preferably phenyl group), each optionally substituted by substituent(s) selected from the group consisting of a halogen atom, a $C_{1-30}$ alkyl group, a $C_{1-30}$ alkoxy group and a halo $C_{1-6}$ alkyl group. Another preferred embodiment of Ar is a phenyl group optionally substituted by substituent(s) selected from the group consisting of a halogen atom, a $C_{1-6}$ alkyl group, a $C_{1-6}$ alkoxy group, and a halo $C_{1-6}$ alkyl group.

The total carbon number of compound (2) is preferably not less than 30, more preferably not less than 35.

$R^5$ and $R^6$ in the aforementioned formula (2) are preferably each independently a $C_{1-30}$ alkyl group optionally substituted by halogen atom(s) (e.g., fluorine atom(s)), more preferably each independently a $C_{1-30}$ alkyl group, further preferably $C_{9-30}$ alkyl group, particularly preferably, the same $C_{14-30}$ alkyl group.

As preferable compound (2), the following compounds can be mentioned.

[Compound (2-1)]

Compound (2) of the aforementioned formula (2), wherein

Ar is a $C_{6-14}$ aryl group optionally substituted by substituent(s) selected from the group consisting of a halogen atom, a cyano group, a $C_{1-30}$ alkyl group, a halo $C_{1-6}$ alkyl group, a $C_{1-30}$ alkoxy group, and a halo $C_{1-6}$ alkoxy group, $R^5$ and $R^6$ are each independently a $C_{1-30}$ alkyl group optionally substituted by halogen atom(s) (e.g., fluorine atom(s)), and the total carbon number is not less than 25 (preferably not less than 30).

[Compound (2-2)]

Compound (2) of the aforementioned formula (2), wherein

Ar is a phenyl group, a 1-naphthyl group, or a 2-naphthyl group (preferably a phenyl group), each optionally substituted by substituent(s) selected from the group consisting of a halogen atom, a $C_{1-30}$ alkyl group, a $C_{1-30}$ alkoxy group, and a halo $C_{1-6}$ alkyl group, $R^5$ and $R^6$ are each independently a $C_{1-30}$ alkyl group, and the total carbon number is not less than 35.

[Compound (2-3)]

Compound (2) of the aforementioned formula (2), wherein

Ar is a phenyl group, $R^5$ and $R^6$ are the same $C_{14-30}$ alkyl group, and the total carbon number is not less than 35.

Specific preferable examples of compound (2) include N,N-dihexadecylaniline, N,N-dioctadecylaniline, N,N-didocosylaniline, and the like.

As base A, a commercially available product may be used as it is, or a compound obtained by a production method shown below can also be used.

(Production Method of Base a (Compound (2)))

Compound (2) can be produced by successively reacting, as shown in the following formula:

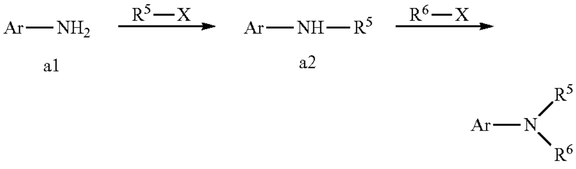

a1 a2 compound (2)

wherein X is a halogen atom, and other symbols are as defined above, aniline derivative (a1) with alkyl halide ($R^5$—X and $R^6$—X) in the presence of a base in a solvent that does not effect the reaction.

When $R^5$ and $R^6$ are the same group, compound (2) can be produced in one step from the aniline derivative (a1).

The amount of the alkyl halide ($R^5$—X or $R^6$—X) to be used is 1 to 2 mol (preferably 1 to 1.2 mol) per 1 mol of the aniline derivative ((a1) or (a2)).

When $R^5$ and $R^6$ are the same group, the amount of alkyl halide to be used is 2 to 4 mol (preferably, 2 to 3 mol) per 1 mol of aniline derivative (a1).

While the reaction solvent is not particularly limited, for example, ether solvents such as tetrahydrofuran, diethoxy ethane, and the like, toluene, dimethylformamide, dimethyl sulfoxide, and the like are preferred.

Examples of the base include sodium hydride, potassium carbonate, potassium tert-butoxide, and the like. The amount of the base to be used is 1 to 2 mol (preferably, 1 to 1.2 mol) per 1 mol of aniline derivative ((a1) or (a2)).

The reaction temperature is preferably room temperature to 180° C.

The reaction time is generally 1 hr to 48 hr.

(Production Method of Base a (a Nitrogen-Containing Aromatic Heterocyclic Compound Having a Total Carbon Number of not Less than 25 and Substituted by the Same or Different, Two or More $C_{1-30}$ Alkyl Groups or $C_{1-30}$ Alkoxy Groups))

The aforementioned nitrogen-containing aromatic heterocyclic compound having a total carbon number of not less than 25 as base (A2) can be produced by successively reacting, as shown in the following formula:

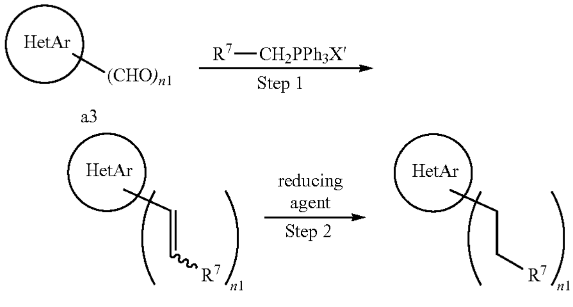

a3 a4 A2 wherein the group represented by the formula:

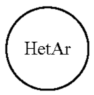

is a nitrogen-containing aromatic heterocyclic group, X' is a halogen atom, $R^7$ is an optionally substituted $C_{1-30}$ alkyl group, and n1 is an integer of two or more, reacting compound (a3) with a phosphonium salt ($R^7$—$CH_2PPh_3X'$) in a solvent that does not effect the reaction in the presence of a base to give compound (a4) (step 1), and reacting the compound with a reducing agent (step 2).

Examples of the base to be used in the aforementioned step 1 include sodium hydride, potassium carbonate, potassium tert-butoxide, and the like.

The amount of the base to be used is 1 to 2 mol (preferably, 1 to 1.2 mol) with respect to the equivalent (1 mol) of formyl group of the compound (a3).

The amount of the phosphonium salt ($R^7$—$CH_2PPh_3X'$) to be used is 1 to 2 mol (preferably, 1 to 1.2 mol) with respect to the equivalent (1 mol) of formyl group of the compound (a3).

The reaction solvent in step 1 is not particularly limited and, for example, ether solvents such as tetrahydrofuran, diethoxy ethane, and the like, aromatic hydrocarbon solvents such as toluene and the like, aliphatic hydrocarbon solvents such as hexane and the like, dimethylformamide, dimethyl sulfoxide, and the like are preferred.

The reaction temperature in step 1 is preferably room temperature to 180° C.

The reaction time in step 1 is generally 0.5 hr to 48 hr.

In the aforementioned step 2, as the reducing agent, for example, in the presence of a metal catalyst, hydrogen, ammonium formate, ammonium chloride, or the like can be used. As the metal catalyst, transition metal catalysts such as Pd/C, Pt/C, and the like are preferred.

The amount of the metal catalyst to be used is 0.001 to 1.0 mol (preferably 0.01 to 0.5 mol) per 1 mol of a double bond of the compound (a4).

While the reaction solvent in step 2 is not particularly limited, for example, hexane, toluene, tetrahydrofuran, ethanol, and the like are preferred, and a mixed solvent thereof may also be used.

For the reduction reaction in step 2, conditions such as normal pressure, moderate pressure, and the like can be appropriately selected according to the progress of the reaction.

The reaction temperature in step 2 is preferably room temperature to 180° C.

The reaction time in step 2 is generally 1 hr to 72 hr.

A preferred embodiment of a compound represented by the aforementioned formula (5) (hereinafter to be also referred to as "compound (5)") is explained in the following.

Each group of compound (5) is explained in the following.

The total carbon number of R and R' is not less than 8, preferably, not less than 16. the total carbon number of R and R' may be not less than 20, not less than 25, or not less than 28. In addition, the total carbon number of R and R' is preferably not more than 32.

R and R' are each independently an optionally substituted $C_{1-30}$ alkyl group, an optionally substituted $C_{3-15}$ cycloalkyl group, or an optionally substituted $C_{6-14}$ aryl group, preferably each independently a $C_{1-30}$ alkyl group optionally substituted by substituent(s) selected from the group consisting of (1) a halogen atom,
(2) a $C_{1-30}$ alkoxy group, and
(3) a halo $C_{1-30}$ alkoxy group;

a $C_{3-15}$ cycloalkyl group optionally substituted by substituent(s) selected from the group consisting of (1) a halogen atom,
(2) a $C_{1-30}$ alkyl group,
(3) a $C_{1-30}$ alkoxy group,
(4) a halo $C_{1-30}$ alkyl group, and
(5) a halo $C_{1-30}$ alkoxy group; or a $C_{6-14}$ aryl group optionally substituted by substituent(s) selected from the group consisting of (1) a halogen atom,
(2) a $C_{1-30}$ alkyl group,
(3) a $C_{1-30}$ alkoxy group,
(4) a halo $C_{1-30}$ alkyl group, and
(5) a halo $C_{1-30}$ alkoxy group, more preferably each independently a $C_{1-30}$ alkyl group; a $C_{3-8}$ cycloalkyl group (e.g., cyclopentyl, cyclohexyl etc.); or a phenyl group optionally substituted by substituent(s) selected from the group consisting of (1) a halogen atom,
(2) a $C_{1-6}$ alkyl group,
(3) a $C_{1-6}$ alkoxy group,
(4) a halo $C_{1-6}$ alkyl group, and
(5) a halo $C_{1-6}$ alkoxy group, further preferably each independently a $C_{1-30}$ alkyl group (preferably $C_{1-18}$ alkyl group such as methyl, butyl, hexyl, octyl, decyl, dodecyl, tetradecyl, hexadecyl, octadecyl, or the like), particularly preferably each independently a $C_{14-30}$ alkyl group.

Preferred compounds (5) are, for example, the following compounds.

[Compound (5-1)]

Compound (5) of the aforementioned formula (5), wherein R and R' are each independently a $C_{1-30}$ alkyl group, and the total carbon number of R and R' is not less than 8.

[Compound (5-2)]

Compound (5) of the aforementioned formula (5), wherein R and R' are each independently a $C_{1-30}$ alkyl group, and the total carbon number of R and R' is not less than 10.

[Compound (5-3)]

Compound (5) of the aforementioned formula (5), wherein R and R' are each independently a $C_{1-30}$ alkyl group optionally substituted by substituent(s) selected from the group consisting of (1) a halogen atom,
(2) a $C_{1-30}$ alkoxy group, and
(3) a halo $C_{1-30}$ alkoxy group;

a $C_{3-15}$ cycloalkyl group optionally substituted by substituent(s) selected from the group consisting of (1) a halogen atom,
(2) a $C_{1-30}$ alkyl group,
(3) a $C_{1-30}$ alkoxy group,
(4) a halo $C_{1-30}$ alkyl group, and
(5) a halo $C_{1-30}$ alkoxy group; or a $C_{6-14}$ aryl group optionally substituted by substituent(s) selected from the group consisting of (1) a halogen atom,
(2) a $C_{1-30}$ alkyl group,
(3) a $C_{1-30}$ alkoxy group,
(4) a halo $C_{1-30}$ alkyl group, and
(5) a halo $C_{1-30}$ alkoxy group, and the total carbon number of R and R' is not less than 16.

[Compound (5-4)]

Compound (5) of the aforementioned formula (5), wherein R and R' are each independently a $C_{1-30}$ alkyl group, or a $C_{6-14}$ aryl group optionally substituted by substituent(s) selected from the group consisting of (1) a halogen atom,
(2) a $C_{1-30}$ alkyl group,
(3) a $C_{1-30}$ alkoxy group,
(4) a halo $C_{1-30}$ alkyl group, and
(5) a halo $C_{1-30}$ alkoxy group, and the total carbon number of R and R' is not less than 16.

[Compound (5-5)]

Compound (5) of the aforementioned formula (5), wherein R and R' are each independently a $C_{1-30}$ alkyl group, a $C_{3-8}$ cycloalkyl group (e.g., cyclopentyl, cyclohexyl etc.), or a phenyl group optionally substituted by substituent(s) selected from the group consisting of (1) a halogen atom,
(2) a $C_{1-6}$ alkyl group,
(3) a $C_{1-6}$ alkoxy group,
(4) a halo $C_{1-6}$ alkyl group and
(5) a halo $C_{1-6}$ alkoxy group, and the total carbon number of R and R' is not less than 16.

[Compound (5-6)]

Compound (5) of the aforementioned formula (5), wherein R and R' are each independently a $C_{1-30}$ alkyl group, and the total carbon number of R and R' is not less than 16.

Specific preferable examples of compound (5) include dibutyl ether, dihexyl ether, dioctyl ether, didecyl ether, didodecyl ether, ditetradecyl ether, dihexadecyl ether, dioctadecyl ether, docosyl ethyl ether, tetradecyloxyethyl tetradecyl ether, cyclopentyl methyl ether, diphenyl ether, octadecyl phenyl ether, and the like. Among them, compound (5) wherein R and R' are each independently a $C_{1-30}$ alkyl group, and the total carbon number of R and R' is not less than 8, such as dibutyl ether, dihexyl ether, dioctyl ether, didecyl ether, didodecyl ether, ditetradecyl ether, dihexadecyl ether, dioctadecyl ether, dinonadecyl ether, and the like, is more preferred, and compound (5) wherein R and R' are each independently a $C_{14-30}$ alkyl group, and the total carbon number of R and R' is not less than 16 and not more than 32, such as ditetradecyl ether, dihexadecyl ether, dioctadecyl ether, dinonadecyl ether, and the like, is more preferred.

Compound (5) in which the total carbon number of R and R' is not more than 7 is not preferable because it has a low boiling point, and it is feared that industrial control of its content is difficult and it may become a catalyst poison.

Preferred embodiments of a compound represented by the formula (1) (hereinafter to be also referred to as "compound (1)") are explained below.

In the following, each group of compound (1) is explained.

$R^1$, $R^2$, $R^3$, and $R^4$ are preferably each independently a phenyl group, a 1-naphthyl group, a 2-naphthyl group, a 2-biphenylyl group, a 3-biphenylyl group, a 4-biphenylyl group, a 1-anthryl group, a 2-anthryl group, a 9-anthryl group, a 3-phenanthryl group, or a 9-phenanthryl group, each substituted by one or more fluorine atoms or fluoro $C_{1-4}$ alkyl groups (e.g., trifluoromethyl groups), more preferably each independently a phenyl group, a 1-naphthyl group, or a 2-naphthyl group, each substituted by one or more fluorine atoms or trifluoromethyl groups, particularly preferably $R^1$, $R^2$, $R^3$, and $R^4$ are all the same and are pentafluorophenyl groups, 2,2',3,3',4',5,5',6,6'-nonafluoro-4-(1,1'-biphenylyl)

groups, 2,3,4,5,6,7,8-heptafluoro-1-naphthyl groups, or 1,3,4,5,6,7,8-heptafluoro-2-naphthyl groups.

A preferred embodiment of A in the $[A-H]^+$ which is a base A-derived cation is the same as the one mentioned above.

As preferable compound (1), the following compounds can be mentioned.

[Compound (1-1)]

Compound (1) of the aforementioned formula (1), wherein $R^1$, $R^2$, $R^3$ and $R^4$ are each independently a phenyl group, a 1-naphthyl group, a 2-naphthyl group, a 2-biphenylyl group, a 3-biphenylyl group, a 4-biphenylyl group, a 1-anthryl group, a 2-anthryl group, a 9-anthryl group, a 3-phenanthryl group, or a 9-phenanthryl group, each substituted by one or more fluorine atoms or fluoro $C_{1-4}$ alkyl groups (e.g., trifluoromethyl group), and A is represented by the aforementioned formula (2), wherein Ar is a $C_{6-14}$ aryl group optionally substituted by substituent(s) selected from the group consisting of a halogen atom, a cyano group, a $C_{1-30}$ alkyl group, a halo $C_{1-6}$ alkyl group, a $C_{1-30}$ alkoxy group, and a halo $C_{1-6}$ alkoxy group, $R^5$ and $R^6$ are each independently a $C_{1-30}$ alkyl group optionally substituted by halogen atom(s) (e.g., fluorine atom(s)), and the total carbon number is not less than 25 (preferably not less than 30).

[Compound (1-2)]

Compound (1) of the aforementioned formula (1), wherein $R^1$, $R^2$, $R^3$ and $R^4$ are each independently a phenyl group, a 1-naphthyl group, or a 2-naphthyl group, each substituted by one or more fluorine atoms or trifluoromethyl groups, and A is represented by the aforementioned formula (2), wherein Ar is a phenyl group, a 1-naphthyl group, or a 2-naphthyl group (preferably a phenyl group), each optionally substituted by substituent(s) selected from the group consisting of a halogen atom, a $C_{1-30}$ alkyl group, a $C_{1-30}$ alkoxy group, and a halo $C_{1-6}$-alkyl group, $R^5$ and $R^6$ are each independently a $C_{1-30}$ alkyl group, and the total carbon number is not less than 35.

[Compound (1-3)]

Compound (1) of the aforementioned formula (1), wherein $R^1$, $R^2$, $R^3$ and $R^4$ are all the same and are pentafluorophenyl groups, 2,2',3,3',4',5,5',6,6'-nonafluoro-4-(1,1'-biphenylyl) groups, 2,3,4,5,6,7,8-heptafluoro-1-naphthyl groups, or 1,3,4,5,6,7,8-heptafluoro-2-naphthyl groups, A is represented by the aforementioned formula (2), wherein Ar is a phenyl group, $R^5$ and $R^6$ are the same $C_{14-30}$ alkyl groups, and the total carbon number is not less than 35.

[Compound (1-4)]

Compound (1) of the aforementioned formula (1), wherein $R^1$, $R^2$, $R^3$ and $R^4$ are each independently a phenyl group, a 1-naphthyl group, a 2-naphthyl group, a 2-biphenylyl group, a 3-biphenylyl group, a 4-biphenylyl group, a 1-anthryl group, a 2-anthryl group, a 9-anthryl group, a 3-phenanthryl group, or a 9-phenanthryl group, each substituted by one or more fluorine atoms or fluoro $C_{1-4}$ alkyl groups (e.g., trifluoromethyl groups), A is a 5- or 6-membered monocyclic nitrogen-containing aromatic heterocyclic compound (e.g., pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazol e, 1,3,4-thiadiazole, triazole, tetrazole, triazine, etc.) substituted by the same or different, two or more $C_{9-30}$ alkyl groups or $C_{9-30}$ alkoxy groups, and the total carbon number is not less than 25 (preferably not less than 30).

[Compound (1-5)]

Compound (1) of the aforementioned formula (1), wherein $R^1$, $R^2$, $R^3$ and $R^4$ are each independently a phenyl group, a 1-naphthyl group, or a 2-naphthyl group, each substituted by one or more fluorine atoms or trifluoromethyl groups, A is pyridine or imidazole, each substituted by the same or different two $C_{14-30}$ alkyl groups or $C_{14-30}$ alkoxy groups (preferably 2,5-dinonadecylpyridine, 2,6-dinonadecylpyridine, 2-nonadecyl-5-octadecylpyridine, 2-nonadecyl-4-octadecyloxypyridine, 2-nonadecyl-6-octadecyloxypyridine, 4-nonadecyl-1-octadecylimidazole, 5-nonadecyl-1-octadecylimidazole, or 2-nonadecyl-1-octadecylimidazole), and the total carbon number is not less than 35.

[Compound (1-6)]

Compound (1) of the aforementioned formula (1), wherein $R^1$, $R^2$, $R^3$ and $R^4$ are all the same and are pentafluorophenyl groups, 2,2',3,3',4',5,5',6,6'-nonafluoro-4-(1,1'-biphenylyl) groups, 2,3,4,5,6,7,8-heptafluoro-1-naphthyl groups, or 1,3,4,5,6,7,8-heptafluoro-2-naphthyl groups (preferably, pentafluorophenyl groups), A is pyridine substituted by the same or different two $C_{14-30}$ alkyl groups or $C_{14-30}$ alkoxy groups (preferably 2,5-dinonadecylpyridine, 2,6-dinonadecylpyridine, 2-nonadecyl-5-octadecylpyridine, 2-nonadecyl-4-octadecyloxypyridine, or 2-nonadecyl-6-octadecyloxypyridine), and the total carbon number is not less than 35.

[Compound (1-7)]

Compound (1) of the aforementioned formula (1), wherein $R^1$, $R^2$, $R^3$ and $R^4$ are each independently a phenyl group, a 1-naphthyl group, a 2-naphthyl group, a 2-biphenylyl group, a 3-biphenylyl group, a 4-biphenylyl group, a 1-anthryl group, a 2-anthryl group, a 9-anthryl group, a 3-phenanthryl group, or a 9-phenanthryl group, each substituted one or more fluorine atoms or fluoro $C_{1-4}$ alkyl groups (e.g., trifluoromethyl group), A is a bicyclic nitrogen-containing aromatic heterocyclic compound (e.g., benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolotriazine, indole, isoindole, 1H-indazole, purine, isoquinoline, quinoline, phthalazine, naphthyridine, quinoxaline, quinazoline, cinnoline, etc.), each substituted the same or different two or more $C_{9-30}$ alkyl groups or $C_{9-30}$ alkoxy groups, and the total carbon number is not less than 25 (preferably not less than 30).

[Compound (1-8)]

Compound (1) of the aforementioned formula (1), wherein $R^1$, $R^2$, $R^3$ and $R^4$ are each independently a phenyl group, a 1-naphthyl group, or a 2-naphthyl group, each substituted by one or more fluorine atoms or trifluoromethyl groups, A is benzimidazole substituted by the same or different two $C_{14-30}$ alkyl groups or $C_{14-30}$ alkoxy groups (preferably 2,6-dinonadecylbenzimidazole, 1,2-dioctadecylbenzimidazole, 1,2-diheptadecylbenzimidazole, 2-heptadecyl-1-octadecylbenzimidazole, or 1-heptadecyl-2-octadecylbenzimidazole), and the total carbon number is not less than 35.

[Compound (1-9)]

Compound (1) of the aforementioned formula (1), wherein $R^1$, $R^2$, $R^3$ and $R^4$ are all the same and are pentafluorophenyl groups, 2,2',3,3',4',5,5',6,6'-nonafluoro-4-(1,1'-biphenylyl) groups, 2,3,4,5,6,7,8-heptafluoro-1-naphthyl groups, or 1,3,4,5,6,7,8-heptafluoro-2-naphthyl groups (preferably pentafluorophenyl groups), A is benzimidazole substituted by the same or different two $C_{14-30}$ alkyl groups or $C_{14-30}$ alkoxy groups (preferably 2,6-dinonadecylbenzimidazole, 1,2-dioctadecylbenzimidazole, 1,2-diheptadecylbenzimidazole, 2-heptadecyl-1-octadecylbenzimidazole, or 1-heptadecyl-2-octadecylbenzimidazole), and the total carbon number is not less than 35.

Specific preferable examples of compound (1) include N,N-dioctadecylanilinium tetrakis(pentafluorophenyl)borate, 2,6-dinonadecylpyridinium tetrakis(pentafluorophenyl)borate, 2-nonadecyl-5-octadecyloxypyridinium tetrakis(pentafluorophenyl)borate, 4-nonadecyl-1-octadecylimidazolium tetrakis(pentafluorophenyl)borate, 5-nonadecyl-1-octadecylimidazolium tetrakis(pentafluorophenyl)borate, 2-nonadecyl-1-octadecylimidazolium tetrakis(pentafluorophenyl)borate, 1-heptadecyl-2-octadecylbenzimidazolium tetrakis(pentafluorophenyl)borate, 2-heptadecyl-1-octadecylbenzimidazolium tetrakis(pentafluorophenyl)borate, and the like.

Specific preferable examples of another compound (1) include 2,6-dinonadecylbenzimidazolium tetrakis(pentafluorophenyl)borate, 1,2-dioctadecylbenzimidazolium tetrakis(pentafluorophenyl)borate, 1,2-diheptadecylbenzimidazolium tetrakis(pentafluorophenyl)borate, 2-heptadecyl-1-octadecylbenzimidazolium tetrakis(pentafluorophenyl)borate, 1-heptadecyl-2-octadecylbenzimidazolium tetrakis(pentafluorophenyl)borate, 2-heptadecyl-1-octadecylbenzimidazolium tetrakis(pentafluorophenyl)borate, and the like.

In the composition of the present invention, base A and A constituting the $[A-H]^+$ in compound (1) are preferably the same. A preferred embodiment of $[A-H]^+$ is, for example, a cation in which proton is added to each of the aforementioned preferred embodiments of base A.

In the composition of the present invention, the content of base A is generally 0.01 to 10 mol, preferably 0.01 to 2 mol, more preferably 0.01 to 1 mol, particularly preferably 0.01 to 0.5 mol, per 1 mol of compound (1).

In the composition of the present invention, the amount ratio of compound (5) and compound (1) is not particularly limited. To improve solubility in aliphatic hydrocarbon solvents, the content of compound (5) is within the range of not less than 0.1 mol, preferably 0.1 to 10 mol, more preferably 0.1 to 3 mol, per 1 mol of compound (1).

The composition of the present invention is soluble in a hydrocarbon solvent at room temperature (15 to 30° C.). In addition, conventionally-known borate-type cocatalysts are insoluble in aliphatic hydrocarbon solvents such as n-hexane and the like. In contrast, the composition of the present invention shows good solubility also in aliphatic hydrocarbon solvents. Therefore, it is useful as a cocatalyst in homogenous polymerization reactions of olefins and dienes.

(Production Method of the Composition of the Present Invention)

The production method of the composition of the present invention (hereinafter to be also referred to as "the production method of the present invention") is explained below.

The composition of the present invention preferably does not contain a hydrogenated borate compound (e.g., hydrogenated tetrakis(pentafluorophenyl)borate) represented by the below-mentioned formula (3), or metal salts of the below-mentioned tetra-substituted borate compounds (e.g., lithium tetrakis(pentafluorophenyl)borate), which can form a complex with an ether compound having a total carbon number of not more than 7 and become a catalyst poison. In addition, the composition of the present invention preferably does not contain an ether compound having a total carbon number of not more than 7 which can be a catalyst poison. Not containing an ether compound having a total carbon number of not more than 7 means that an ether compound having a total carbon number of not more than 7 is not detected as a result of $^1H$-NMR analysis.

The production method of the present invention (hereinafter to be also referred to as "the production method 1 of the present invention") characteristically includes a step of reacting a hydrogenated borate compound represented by the following formula (3):

(3)

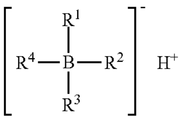

wherein $R^1$, $R^2$, $R^3$, and $R^4$ are as defined above (hereinafter to be also referred to as "compound (3)") with the aforementioned base A, and uses base A in an amount exceeding 1 mol with respect to 1 mol of compound (3).

Examples of compound (3) to be used as a starting material in the above-mentioned production method include known compounds such as hydrogenated tetrakis(pentafluorophenyl)borate, hydrogenated tetrakis(nonafluoro[1,1'-biphenyl]-4-yl)borate, hydrogenated tetrakis(heptafluoro-2-naphthyl)borate, hydrogenated [3,5-bis(trifluoromethyl)phenyl]borate, and the like.

The production method of compound (3) is not particularly limited and is, for example, a method including treating a compound represented by the formula (4):

(4)

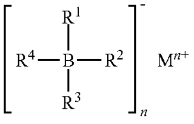

wherein $R^1$, $R^2$, $R^3$, and $R^4$ are each independently a $C_{6-14}$ aryl group substituted by one or more fluorine atoms or fluoro $C_{1-4}$ alkyl groups, M is an alkali metal such as lithium, potassium, sodium, or the like, or an alkaline earth metal such as calcium, magnesium, barium, or the like, and n is 1 or 2 (hereinafter to be also referred to as "compound (4)") with protonic acid, or the like.

As the aforementioned compound (4) used for the production of compound (3), a commercially available product or a purified product may be used, or one prepared by a method known per se (see, for example, Angew. Chem. Int. Ed., 2009, 48(40), 7444-7447) may also be used.

The solvent to be used in the production of compound (3) is not particularly limited, but it is desirable to use ether solvents such as diethyl ether, tert-butyl methyl ether, cyclopentyl methyl ether, diisopropyl ether, and the like, halogenated solvents such as dichloromethane, chloroform, and the like, aromatic hydrocarbon solvents such as toluene, benzene, and the like, and aliphatic hydrocarbon solvents such as n-hexane, isohexane, n-heptane, octane, cyclohexane, methylcyclohexane, and the like. In addition, these solvents may be used alone or in combination.

The protonic acid to be used in the treatment of compound (4) is not particularly limited, and examples thereof include hydrochloric acid, sulfuric acid, nitric acid, hydrobromic acid, hydroiodic acid, and the like.

The amount of the protonic acid to be used for the production of compound (3) is desirably 1 mol per 1 mol of compound (4). When not less than 1 mol of protonic acid is used, the organic phase is preferably washed with water until the pH of the aqueous phase after washing with water becomes not less than 3, so that the protonic acid used will not remain in the organic phase after the treatment. When the pH of the aqueous phase is less than 3, it is feared that the protonic acid salt used remains in the organic phase, and a protonic acid salt of the base A is generated in the reaction with the base A and remains in the composition of the present invention to be a catalyst poison during polymerization.

In the Production Method 1 of the present invention, the solution of compound (3) prepared as mentioned above can be used as it is for the reaction with base A.

As the base A to be used in the Production Method 1 of the present invention, the aforementioned compound having a total carbon number of not less than 25 (preferably not less than 30, more preferably not less than 35) can be mentioned. Specific examples of base A include nitrogen-containing aromatic heterocyclic compounds such as 2,5-dinonadecylpyridine, 2,6-dinonadecylpyridine, 2-nonadecyl-5-octadecylpyridine, 2-nonadecyl-4-octadecyloxypyridine, 2-nonadecyl-6-octadecyloxypyridine, 4-nonadecyl-1-octadecylimidazole, 5-nonadecyl-1-octadecylimidazole, 2-nonadecyl-1-octadecylimidazole, and the like; aromatic amine compounds such as N,N-dihexadecylaniline, N,N-dioctadecylaniline, N,N-dinonadecyl aniline, N,N-didocosylaniline, and the like, and the like.

Among them, a composition containing base A and compound (1) obtained by reacting compound (3) and base A having two or more $C_{9-30}$ alkyl groups (preferably $C_{14-30}$ alkyl groups) or $C_{9-30}$ alkoxy groups (preferably $C_{14-30}$ alkoxy groups) is also soluble in aliphatic hydrocarbon solvents.

In the Production Method 1 of the present invention, base A is used in an amount exceeding 1 mol per 1 mol of compound (3). In this way, it is possible to suppress unreacted compound (3) from remaining in the resultant product composition. The amount of base A to be used is within the range of 1.01 to 5.0 mol, preferably 1.01 to 2.0 mol, particularly preferably 1.01 to 1.5 mol, per 1 mol of compound (3). When the amount of base A is not more than 1.0 mol, it is feared that an ether solvent (that is, ether compound) having a total carbon number of not more than 7 or water-added compound (3) remains in the resultant product composition, and the ether compound having a total carbon number of not more than 7 or water-added compound (3) acts as a catalyst poison when used as a cocatalyst for polymerization. When the amount of base A to be used is 1 mol with respect to compound (3), the solubility of the composition of the present invention in aliphatic hydrocarbon solvents decreases.

The reaction temperature and the time in the Production Method 1 of the present invention are not particularly limited. The reaction temperature is generally 10° C. to 40° C., preferably 10° C. to 35° C., more preferably room temperature (15° C. to 30° C.), and the time is not less than 10 min.

After completion of the reaction of compound (3) and the base A, the reaction mixture is dehydrated with a desiccant such as anhydrous sodium sulfate, anhydrous magnesium sulfate, or the like, and then the solvent is removed, whereby a composition containing base A and compound (1) can be obtained.

In another method, after completion of the reaction of compound (3) and base A, a part of the reaction solvent is evaporated or solvent dilution or solvent evaporation (solvent substitution) is performed once or multiple times, whereby a solution of a composition containing base A and compound (1) can be obtained.

A preferred embodiment of the aforementioned compound (3) is similar to the preferred embodiment of the anionic part (anionic part of compound (1-1) to compound (1-9)) in the aforementioned compound (1).

As preferable compound (4), the following compounds can be mentioned.

[Compound (4-1)]

Compound (4) of the aforementioned formula (4), wherein $R^1$, $R^2$, $R^3$, and $R^4$ are each independently a phenyl group, a 1-naphthyl group, a 2-naphthyl group, a 2-biphenylyl group, a 3-biphenylyl group, a 4-biphenylyl group, a 1-anthryl group, a 2-anthryl group, a 9-anthryl group, a 3-phenanthryl group, or a 9-phenanthryl group, each substituted by one or more fluorine atoms or fluoro $C_{1-4}$ alkyl groups (e.g., trifluoromethyl groups), M is lithium, sodium, potassium, calcium, magnesium, or barium, and n is 1 or 2.

[Compound (4-2)]

Compound (4) of the aforementioned formula (4), wherein $R^1$, $R^2$, $R^3$ and $R^4$ are each independently a phenyl group, a 1-naphthyl group, or a 2-naphthyl group, each substituted by one or more fluorine atoms or trifluoromethyl groups, M is lithium, sodium, or potassium, and n is 1.

[Compound (4-3)]

Compound (4) of the aforementioned formula (4), wherein $R^1$, $R^2$, $R^3$, and $R^9$ are all the same and are pentafluorophenyl groups, 2,2',3,3',4',5,5',6,6'-nonafluoro-4-(1,1'- biphenylyl) groups, 2,3,4,5,6,7,8-heptafluoro-1-naphthyl groups, or 1,3,4,5,6,7,8-heptafluoro-2-naphthyl groups, M is lithium or sodium, and n is 1.

Specific preferable examples of compound (4) include known compounds such as lithium tetrakis(pentafluorophenyl)borate, sodium tetrakis(pentafluorophenyl)borate, lithium tetrakis(nonafluoro[1,1'-biphenyl]-4-yl)borate, lithium tetrakis(heptafluoro-2-naphthyl)borate, lithium [3,5-bis(trifluoromethyl)phenyl]borate, sodium [3,5-bis(trifluoromethyl)phenyl]borate, lithium tetrakis(2,3,4,5,6,7,8-heptafluoro-1-naphthyl)borate, lithium tetrakis(1,3,4,5,6,7,8-heptafluoro-2-naphthyl)borate, sodium tetrakis(2,3,4,5,6,7,8-heptafluoro-1-naphthyl)borate, sodium tetrakis(1,3,4,5,6,7,8-heptafluoro-2-naphthyl)borate, and the like.

As another preferred embodiment of the production method of the present invention, the following production methods (Production Method 2 and Production Method 3 of the present invention) can be mentioned.

(Production Method 2 of the Present Invention)

The composition of the present invention can be produced by mixing and stirring base A, protonic acid, and the aforementioned compound (4) in any order, successively or simultaneously in a solvent that does not affect the reaction, as shown in the following formula:

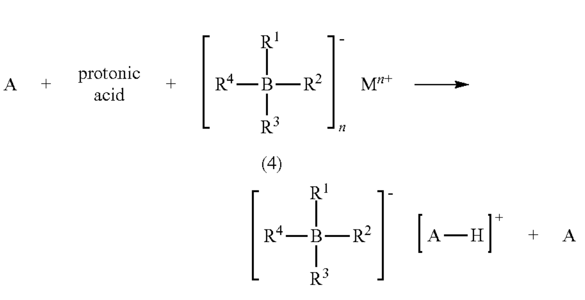

(4)

(1)

wherein each symbol is as defined above.

The amounts of the base A, protonic acid, and compound (4) to be used in the Production Method 2 of the present invention, the reaction solvent, the reaction temperature, the reaction time and the like are similar to those in the 0.5 aforementioned Production Method 1 of the present invention.

(Production Method 3 of the Present Invention)

The composition of the present invention can be produced by mixing and stirring 1 mol of base A and 1 mol of protonic acid, per 1 mol of compound (4), and the aforementioned compound (4) in any order, successively or simultaneously in a solvent that does not affect the reaction, and then mixing the aforementioned compound (5), as shown in the following formula:

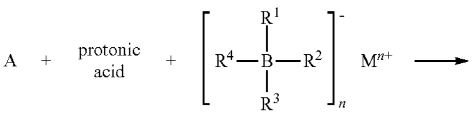

(4)

-continued

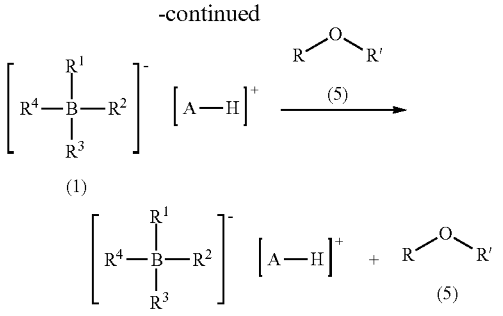

(5)

(1)

(1) (5)

wherein each symbol is as defined above.

The amount of compound (5) to be used in the Production Method 3 of the present invention is within the range of not less than 0.1 mol, preferably 0.1 to 10 mol, more preferably 0.1 to 3 mol, per 1 mol of compound (1) (compound (4)). When the amount of compound (5) is less than 0.1 mol, the solubility of the composition of the present invention decreases. The kinds and amounts of the base A, protonic acid, and compound (4) to be used in the Production Method 3 of the present invention, the reaction solvent, the reaction temperature, the reaction time, and the like are similar to those in the aforementioned Production Method 1 of the present invention.

The composition of the present invention contains base A or compound (5), and compound (1), soluble (or easily soluble) in hydrocarbon solvents, particularly aliphatic hydrocarbon solvents, and does not contain a compound that could be a catalyst poison such as basic and highly nucleophilic amine compound, protonic acid salt of base A, ether compound with a total carbon number of not more than 7, and the like. Therefore, it is useful as a cocatalyst for polymerization of olefins and dienes.

The present invention includes a production method of a polymer by polymerizing at least one kind of monomer selected from the group consisting of an olefin and a diene, by using the composition of the present invention as a cocatalyst. Polymerizing at least one kind of monomer selected from the group consisting of an olefin and a diene, by using a borate compound similar to compound (1) of the present invention as a cocatalyst is known as described in, for example, Patent document 2. Therefore, the production method of the polymer of the present invention can be performed by referring to the production method of the polymer described in the aforementioned Patent document 2, except for using the composition of the present invention as a cocatalyst.

EXAMPLE

The present invention is specifically explained in detail in the following by referring to Production Examples and Example; however, the present invention is not limited to those Production Examples and Examples alone. % means mol/mol % for yield and wt % for others unless particularly indicated. The room temperature refers to a temperature of from 15° C. to 30° C. unless particularly indicated.

For the analysis, the following instrument was used.

$^1$H-NMR and $^{19}$F-NMR: 400YH (JEOL) manufactured by JEOL Ltd.

Unless particularly indicated, the solvents and reagents used in the following Examples were purchased from distributors such as Sigm-Aldrich, Tokyo Chemical Industry Co., Ltd., FUJIFILM Wako Pure Chemical Corporation, JUNSEI CHEMICAL CO., LTD., KANTO CHEMICAL CO., INC., Combi-Blocks, Inc., and the like. The deuterated solvents used for NMR measurement were purchased from Cambridge Isotope Laboratories.

Example 1

Composition Containing N,N-dioctadecylanilinium tetrakis (pentafluorophenyl)borate and N,N-dioctadecylaniline N,N-Dioctadecylaniline (4.3 g, 7.2 mmol) and a lithium tetrakis(pentafluorophenyl)borate tri(diethyl ether) complex (manufactured by AGC Wakasa Chemicals Co., Ltd.) (5.0 g, 5.5 mmol) were suspended in n-hexane (50 mL). Then, 1.0 M hydrogen chloride-diethyl ether solution (5.5 mL) was added dropwise, and the mixture was stirred at room temperature for 3 hr. The obtained suspension was filtered, and the filtrate was concentrated under reduced pressure at 50° C. to give the title composition (7.31 g).

$^1$H NMR ($CDCl_3$) δ: 0.86-0.89 (6H, m), 1.17-1.48 (27H, m), 3.41 (4H, t), 7.23-7.26 (2H, m), 7.45-7.46 (3H, m);

$^{19}$F NMR ($CDCl_3$) δ: −133.8 (8F, t), −163.4 (4F, t), −167.4 (8F, t).

It was confirmed that the composition obtained in Example 1 dissolves in n-hexane and cyclohexane at a concentration of 20 wt %.

Example 2

Composition Containing N,N-dioctadecylanilinium tetrakis (pentafluorophenyl)borate and N,N-dioctadecylaniline To N,N-dioctadecylanilinium tetrakis(pentafluorophenyl) borate (128 mg, 0.1 mmol) was added n-hexane (512 mg), and the mixture was stirred (concentration 20 wt %). To the obtained two-layer separation solution was added N,N-dioctadecylaniline (24 mg, 0.04 mmol), and the mixture was stirred to give a homogeneous n-hexane solution of a composition containing N,N-dioctadecylanilinium tetrakis (pentafluorophenyl)borate and N,N-dioctadecylaniline. n-Hexane was evaporated under reduced pressure and dried under reduced pressure at 50° C. to give the title composition.

$^1$H NMR ($CDCl_3$) δ: 0.8 (6H, t), 1.10-1.50 (64H, m), 3.36-3.40 (4H, m), 7.10-7.12 (2H, m), 7.33-7.51 (3H, m);

$^{19}$F NMR ($CDCl_3$) δ: −133.8 (8F, t), −163.4 (4F, t), −167.5 (8F, t).

It was confirmed that the composition obtained in Example 2 dissolves in n-hexane at a concentration of 20 wt %.

Production Example 1

Synthesis of 2,6-bis(nonadecen-1-yl)pyridine

To a mixture of pyridine-2,6-dicarbaldehyde (1.0 g, 7.4 mmol), octadecyltriphenylphosphonium bromide (10 g, 17 mmol), and tetrahydrofuran (100 mL) was added potassium tert-butoxide (2.0 g, 18 mmol) at room temperature. The mixture was stirred at 60° C. for 2 hr, and allowed to cool to room temperature. The reaction mixture was carefully added to water, and the mixture was extracted with ethyl acetate. The organic phase was washed with saturated brine solution, dried over anhydrous sodium sulfate, and the solvent was evaporated under reduced pressure. The obtained residue was suspended in diethyl ether, insoluble material was filtered off, and the filtrate was concentrated under reduced pressure. The residue was purified by silica gel column chromatography (n-hexane/ethyl acetate=98/2 to 90/10) to give 2,6-bis(nonadecen-1-yl)pyridine (E/Z mixture; 3.9 g, 86%).

$^1$H NMR ($CDCl_3$) δ: 0.88 (6H, t), 1.20-1.48 (60H, m), 2.56-2.62 (4H, m), 5.82-5.89 (1H, m), 6.42-6.49 (2H, m), 7.04 (2H, d), 7.26-7.35 (1H, m), 7.53-7.57 (1H, m).

Production Example 2

Synthesis of 2,6-di(nonadecyl)pyridine

A mixture of 2,6-bis(nonadecen-1-yl)pyridine (E/Z mixture; 3.5 g, 5.8 mmol) obtained in Production Example 1, 10% Pd/C (containing water (50%); 0.70 g), and tetrahydrofuran (100 mL) was stirred under a hydrogen atmosphere at room temperature and normal pressure for 15 hr. The mixture was filtered, and the filtrate was concentrated under reduced pressure. The obtained residue was purified by silica gel column chromatography (n-hexane/ethyl acetate=95/5) to give 2,6-di(nonadecyl)pyridine (3.0 g, 85%).

$^1$H NMR ($CDCl_3$) δ: 0.88 (6H, t), 1.17-1.40 (64H, m), 1.65-1.70 (4H, m), 2.72-2.76 (4H, m), 6.93 (2H, d), 7.48 (1H, t).

Production Example 3

Synthesis of 2,6-di(nonadecyl)pyridine hydrochloride

To an n-hexane solution (30 mL) of 2,6-di(nonadecyl) pyridine (3.0 g, 4.9 mmol) obtained in Production Example 2 was added 1 M hydrogen chloride-diethyl ether solution (10 mL) at room temperature, and the mixture was stirred for 1 hr. The obtained precipitate was collected by filtration, washed with n-hexane, and dried under reduced pressure to give 2,6-di(nonadecyl)pyridine hydrochloride (3.0 g, 94%).

$^1$H NMR ($CDCl_3$) δ: 0.88 (6H, t), 1.24-1.45 (64H, m), 1.79-1.87 (4H, m), 3.32 (4H, br), 7.41 (2H, d), 8.08 (1H, br).

Production Example 4

Synthesis of 2,6-di(nonadecyl)pyridinium tetrakis(pentafluorophenyl)borate 2,6-di(nonadecyl)pyridine hydrochloride (0.50 g, 0.77 mmol) obtained in Production Example 3 and lithium tetrakis(pentafluorophenyl)borate mono(diethyl ether) complex (0.59 g, 0.78 mmol) was suspended in dichloromethane (20 mL), and the mixture was stirred at room temperature for 1 hr. The obtained suspension was filtered, and the filtrate was concentration under reduced pressure at 50° C. to give 2,6-di(nonadecyl)pyridinium tetrakis(pentafluorophenyl) borate (0.99 g, 99%).

$^1$H NMR ($CDCl_3$) δ: 0.85-0.89 (6H, m), 1.23-1.35 (64H, m), 1.72-1.76 (4H, m), 2.94-2.98 (4H, t), 7.57 (2H, d), 8.27 (1H, dd);

$^{19}$F NMR ($CDCl_3$) δ: −133.3 (8F, t), −163.2 (4F, t), −167.7 (8F, t).

Example 3

Composition Containing 2,6-di(nonadecyl)pyridinium tetrakis(pentafluorophenyl)borate and 2,6-di(nonadecyl)pyridine To 2,6-di(nonadecyl)pyridinium tetrakis(pentafluorophenyl)borate (129 mg, 0.1 mmol) obtained in Production Example 4 was added 2,6-di(nonadecyl)pyridine (12.9 mg, 0.02 mmol) obtained in Production Example 2, and n-hexane (0.52 g) was further added. The mixture was stirred for 1 hr to give a homogeneous n-hexane solution. The solvent was evaporated under reduced pressure to give the title composition.

$^1$H NMR ($CDCl_3$) δ: 0.88 (6H, t), 1.20-1.50 (64H, m), 1.67-1.73 (4H, m), 2.88 (4H, t), 7.38 (2H, d), 8.03 (1H, dd);

$^{19}$F NMR ($CDCl_3$) δ: −133.9 (8F, t), −163.6 (4F, t), −167.7 (8F, t).

It was confirmed that the composition obtained in Example 3 dissolves in n-hexane at a concentration of 20 wt %.

Production Example 5

Synthesis of 2-(nonadecen-1-yl)-5-octadecoxypyridine

To a mixture of 5-octadecoxypyridine-2-carbaldehyde (2.0 g, 5.3 mmol), octadecyltriphenylphosphonium bromide (7.0 g, 12 mmol), and tetrahydrofuran (100 mL) was added potassium tert-butoxide (1.4 g, 12 mmol) at room temperature. The mixture was stirred at 60° C. for 2 hr, and allowed to cool to room temperature. The reaction mixture was carefully added to water, and the mixture was extracted with ethyl acetate. The organic phase was washed with saturated brine solution, dried over anhydrous sodium sulfate, and concentrated under reduced pressure. The obtained residue was suspended in diethyl ether, insoluble material was filtered off, and the filtrate was concentrated under reduced pressure. The residue was purified by silica gel column chromatography (n-hexane/ethyl acetate=98/2 to 90/10) to give 2-(nonadecen-1-yl)-5-octadecoxypyridine (E/Z mixture; 3.1 g, 95%).

$^1$H NMR ($CDCl_3$) δ: 0.87 (6H, t), 1.24-1.50 (60H, m), 1.76-1.80 (2H, m), 2.48-2.54 (2H, m), 3.95-4.00 (2H, m), 7.71-7.78 (1H, m), 6.36-6.40 (1H, m), 7.13-7.18 (2H, m), 8.2-8.27 (1H, m).

Production Example 6

Synthesis of 2-nonadecyl-5-octadecoxypyridine

A mixture of 2-(nonadecen-1-yl)-5-octadecoxypyridine (E/Z mixture; 2.5 g, 4.1 mmol) obtained in Production Example 5, 10% Pd/C (containing water (50%); 0.70 g), n-hexane (100 mL), and tetrahydrofuran (100 mL) was stirred under a hydrogen atmosphere at room temperature and normal pressure for 15 hr. The reaction mixture was filtered, and the filtrate was concentrated under reduced pressure. The obtained residue was purified by silica gel column chromatography (n-hexane/ethyl acetate=95/5) to give 2-nonadecyl-5-octadecoxypyridine (1.0 g, 40%).

$^1$H NMR ($CDCl_3$) δ: 0.87 (6H, t), 1.17-1.40 (64H, m), 1.42-1.76 (4H, m), 2.67-2.72 (2H, m), 3.95 (1H, t), 7.02 (2H, d), 7.10 (2H, dd), 8.19 (1H, d).

Example 4

Composition Containing 2-nonadecyl-5-octadecoxypyridinium tetrakis(pentafluorophenyl)borate and 2-nonadecyl-5-octadecoxypyridine 2-nonadecyl-5-octadecoxypyridine (0.65 g, 1.1 mmol) obtained in Production Example 6 and lithium tetrakis (pentafluorophenyl)borate tri(diethyl ether) complex (0.80 g, 0.88 mmol) was suspended in cyclohexane (20 mL), 1 M hydrogen chloride-diethyl ether solution (0.88 mL, 0.88 mmol) was added, and the mixture was stirred at room temperature for 3 hr. Insoluble material was removed by filtration, and the filtrate was dried under reduced pressure at 45° C. to give the title composition.

$^1$H NMR ($CDCl_3$) δ: 0.88 (3H, t), 1.22-1.44 (64H, m), 1.69-1.86 (4H, m), 2.93 (2H, t), 4.02 (2H, t), 7.60 (1H, d), 7.84 (1H, dd), 7.90 (1H, d).

It was confirmed that the composition obtained in Example 4 dissolves in n-hexane at a concentration of 20 wt %.

Production Example 7

Synthesis of 1-octadecylimidazole-2-carbaldehyde

A mixture of 1H-imidazole-2-carbaldehyde (2.0 g, 21 mmol), 1-bromooctadecane (7.5 g, 22 mmol), potassium carbonate (4.5 g, 33 mmol), and N,N-dimethylformamide was stirred at room temperature for 15 hr. The mixture was poured into water, and the mixture was extracted with ethyl acetate. The organic phase was dried over anhydrous sodium sulfate and concentrated under reduced pressure. The residue was purified by silica gel chromatography (n-hexane-ethyl acetate=98/2 to 90/10) to give 1-octadecylimidazole-2-carbaldehyde (6.45 g, 89%).

$^1$H NMR ($CDCl_3$) δ: 0.88 (3H, t), 1.24-1.30 (34H, m), 1.75-1.79 (2H, m), 4.36-4.40 (2H, m), 7.15 (1H, s), 7.29 (1H, d), 9.81 (1H, s).

Production Example 8

Synthesis of 2-(nonadecen-1-yl)-1-octadecylimidazole

To a mixture of 1-octadecylimidazole-2-carbaldehyde (5.0 g, 14 mmol) obtained in Production Example 7, octadecyltriphenylphosphonium bromide (10 g, 16.8 mmol) and tetrahydrofuran (50 mL) was added potassium tert-butoxide (2.0 g, 17.8 mmol) at room temperature. The mixture was stirred at 60° C. for 2 hr, and allowed to cool to room temperature. The reaction mixture was carefully added to water, and the mixture was extracted with ethyl acetate. The organic phase was washed with saturated brine solution, dried over anhydrous sodium sulfate, and concentrated under reduced pressure. The obtained residue was suspended in diethyl ether, insoluble material was filtered off, and the filtrate was concentrated under reduced pressure. The residue was purified by silica gel column chromatography (n-hexane/ethyl acetate=98/2 to 90/10) to give 2-(nonadecen-1-yl)-1-octadecylimidazole (E/Z mixture; 7.5 g, 89%).

$^1$H NMR ($CDCl_3$) δ: 0.88 (6H, t), 1.11-1.73 (64H, m), 2.20-2.26 (2H, m), 3.85-3.90 (2H, m), 6.11-6.23 (1H, m), 6.67-6.74 (1H, m), 6.81-6.82 (1H, m), 6.98-7.09 (1H, m).

Production Example 9

Synthesis of 2-nonadecyl-1-octadecylimidazole

A mixture of 2-(nonadecen-1-yl)-1-octadecylimidazole (E/Z mixture; 1.5 g, 2.6 mmol) obtained in Production Example 8, 10% Pd/C (containing water (50%); 0.30 g), and tetrahydrofuran (100 mL) was stirred under a hydrogen atmosphere at room temperature and normal pressure for 15 hr. The mixture was filtered, and the filtrate was concentrated under reduced pressure. The obtained residue was purified by silica gel column chromatography (n-hexane/ethyl acetate=95/5) to give 2-nonadecyl-1-octadecylimidazole (1.0 g, 67%).

$^1$H NMR ($CDCl_3$) δ: 0.88 (6H, t), 1.25-1.75 (66H, m), 2.60-2.64 (2H, m), 3.79-3.82 (2H, m), 6.79 (1H, d), 6.93 (1H, d).

Production Example 10

Synthesis of 2-nonadecyl-1-octadecylimidazole hydrochloride

To a suspension of 2-nonadecyl-1-octadecylimidazole (0.88 g, 1.5 mmol) obtained in Production Example 9 and n-hexane (100 mL) was added 1 M hydrogen chloride-diethyl ether solution (10 mL) at room temperature, and the mixture was stirred for 1 hr. The solvent in the obtained suspension was evaporated under reduced pressure to give 2-nonadecyl-1-octadecylimidazole hydrochloride (0.98 g, 100%).

$^1$H NMR ($CDCl_3$) δ: 0.88 (6H, t), 1.25-1.40 (62H, m), 1.80-1.88 (4H, m), 3.02-3.07 (2H, t), 3.96-4.00 (2H, t), 6.97 (1H, d), 7.29 (1H, d).

Production Example 11

Synthesis of 2-nonadecyl-1-octadecylimidazolium tetrakis(pentafluorophenyl)borate 2-nonadecyl-1-octadecylimidazole hydrochloride (0.98 g, 1.57 mmol) obtained in Production Example 10 and lithium tetrakis(pentafluorophenyl)borate diethyl ether complex (1.19 g, 1.57 mmol) was suspended in cyclohexane (30 mL), and the mixture was stirred at room temperature for 1 hr. Brine was added and the organic phase was washed, dried over anhydrous magnesium sulfate, and concentrated under reduced pressure. The concentrate was dried under reduced pressure at 45° C. to give 2-nonadecyl-1-octadecylimidazolium tetrakis(pentafluorophenyl)borate (0.82 g, 94%).

$^1$H NMR ($CDCl_3$) δ: 0.88 (6H, t), 1.25-1.43 (62H, m), 1.66-1.82 (4H, m), 2.81 (2H, t), 3.94 (2H, t), 6.99 (1H, d), 7.03 (1H, d);

$^{19}$F NMR ($CDCl_3$) δ: −133.9 (8F, t), −164.1 (4F, t), −167.9 (8F, t).

Example 5

Composition Containing 2-nonadecyl-1-octadecylimidazole and 2-nonadecyl-1-octadecylimidazolium tetrakis(pentafluorophenyl)borate 2-Nonadecyl-1-octadecylimidazole (24.1 mg, 0.04 mmol) obtained in Production Example 9 and 2-nonadecyl-1-octadecylimidazolium tetrakis(pentafluorophenyl)borate (126.7 mg, 0.1 mmol) obtained in Production Example 11 were dissolved in cyclohexane (0.5 mL) to give a 20 wt % cyclohexane solution. This solution was concentrated under reduced pressure to give the title composition.

1H NMR ($CDCl_3$) δ: 0.88 (6H, t), 1.22-1.33 (62H, m), 1.66-1.82 (4H, m), 2.81 (2H, t), 3.94 (2H, t), 6.99 (1H, d), 7.03 (1H, d);

$^{19}$F NMR ($CDCl_3$) δ: −133.9 (8F, t), −164.1 (4F, t), −167.9 (8F, t).

It was confirmed that the composition obtained in Example 5 dissolves in cyclohexane at a concentration of 20 wt %.

Production Example 12

Synthesis of 2-heptadecyl-1-octadecylbenzimidazole

2-Heptadecyl-1H-benzimidazole (1.5 g, 4.2 mmol) obtained by a method similar to the example known per se (e.g., Australian Journal of Chemistry (2015), 68(1), 145-155), potassium carbonate (1.1 g, 8.0 mmol), and 1-octadecyl bromide (1.5 g, 4.5 mmol) were mixed in DMF (30 mL), and the mixture was stirred at 60° C. for 16 hr. The reaction mixture was cooled to room temperature and poured into water. The suspension was stirred at room temperature for 1 hr, and the precipitate was collected by filtration. The obtained solid was dried under reduced pressure at 80° C. to give the title compound (2.25 g, 88%).

$^1$H NMR ($CDCl_3$) δ: 0.88-0.92 (6H, m), 1.25-1.45 (60H, m), 1.75-1.93 (4H, m), 2.84 (2H, t), 4.08 (2H, t), 7.196-7.30 (3H, m), 7.70-7.73 (1H, m).

Production Example 13

2-Heptadecyl-1-octadecylbenzimidazolium tetrakis(pentafluorophenyl)borate

2-Heptadecyl-1-octadecylbenzimidazole (0.61 g, 1.0 mmol) obtained in Production Example 12 and lithium tetrakis(pentafluorophenyl)borate tri(diethyl ether) complex (0.91 g, 1.0 mmol) was suspended in cyclohexane (30 mL), a 1.0 M hydrogen chloride-diethyl ether solution (1.0 mL) was added dropwise, and the mixture was stirred at room temperature for 3 hr. The obtained suspension was filtered, and the filtrate was concentrated under reduced pressure at 50° C. to give the title compound (1.22 g, 80%).

$^1$H NMR ($CDCl_3$) δ: 0.88 (6H, t), 1.22-1.44 (60H, m), 1.86-1.92 (4H, m), 3.10 (2H, t), 4.28 (2H, t), 7.58-7.70 (4H, m);

$^{19}$F NMR ($CDCl_3$) δ: −134.0 (8F, m), −163.7 (4F, t), −167.7 (8F, t).

Example 6

Composition Containing 2-heptadecyl-1-octadecylbenzimidazolium tetrakis(pentafluorophenyl)borate and 2-heptadecyl-1-octadecylbenzimidazole 2-Heptadecyl-1-octadecylbenzimidazolium tetrakis(pentafluorophenyl)borate (500 mg, 0.4 mmol) obtained in Production Example 13 and 2-heptadecyl-1-octadecylbenzimidazole (47 mg, 0.15 mmol) obtained in Production Example 12 were mixed and n-hexane was added. The mixture was concentrated under reduced pressure and dried under reduced pressure for 16 hr to give the title composition.

$^1$H NMR ($CDCl_3$) δ: 0.88 (6H, t), 1.16-1.41 (60H, m), 1.84-1.91 (4H, m), 3.06 (2H, t), 4.25 (2H, t), 7.44-7.63 (4H, m);

$^{19}$F NMR ($CDCl_3$) δ: −133.9 (8F, d), −164.0 (4F, t), −167.9 (8F, t).

It was confirmed that the composition obtained in Example 6 dissolves in n-hexane at a concentration of 10 wt %.

Example 7

Composition Containing 2-nonadecyl-5-octadecoxypyridinium tetrakis(pentafluorophenyl)borate and tetradecyl ether 2-Nonadecyl-5-octadecoxypyridinium tetrakis(pentafluorophenyl)borate (39 mg, 0.03 mmol), tetradecyl ether (12.3 mg, 0.03 mmol), and n-hexane (351 mg) were mixed and stirred at 25° C. The mixture became a homogeneous solution. The mixture was concentrated under reduced pressure and dried under reduced pressure at 50° C. to give the title composition.

$^1$H NMR ($CDCl_3$) δ: 0.86-0.90 (12H, m), 1.23-1.84 (114H, m), 2.91 (2H, t), 3.41 (4H, t), 4.03 (2H, t), 7.62 (1H, d), 7.85-7.89 (2H, m);

$^{19}$F NMR ($CDCl_3$) δ: −134.1 (8F,t), −163.4 (4F,t), −167.4 (8F, t).

It was confirmed that the composition obtained in Example 7 dissolves in n-hexane at a concentration of 10 wt %.

Example 8

Composition Containing 2,6-di(nonadecyl)pyridinium tetrakis(pentafluorophenyl)borate and tetradecyl ether 2,6-Di(nonadecyl)pyridinium tetrakis(pentafluorophenyl) borate (39 mg, 0.03 mmol) obtained in Production Example 4, tetradecyl ether (12.3 mg, 0.03 mmol), and n-hexane (351 mg) were mixed and stirred at 25° C. The mixture became a homogeneous solution. The mixture was concentrated under reduced pressure and dried under reduced pressure at 50° C. to give the title composition.

$^1$H NMR ($CDCl_3$) δ: 0.88 (12H, t), 1.25-1.40 (76H, m), 1.52-1.60 (4H, m), 1.70-1.78 (4H, m), 2.97 (4H, t), 3.39 (4H, t), 7.57 (2H, d), 8.28 (1H, t);

$^{19}$F NMR ($CDCl_3$) δ: −138.8 (8F,s), −163.6 (4F,t), −167.7 (8F, t).

It was confirmed that the composition obtained in Example 8 dissolves in n-hexane at a concentration of 10 wt %.

Example 9

Composition Containing 2-heptadecyl-1-octadecylbenzimidazolium tetrakis(pentafluorophenyl)borate and tetradecyl ether 2-Heptadecyl-1-octadecylbenzimidazolium tetrakis(pentafluorophenyl)borate (39 mg, 0.03 mmol) obtained in Production Example 13, tetradecyl ether (12.3 mg, 0.03 mmol), and n-hexane (351 mg) were mixed and stirred at 25° C. The mixture became a homogeneous solution. The mixture was concentrated under reduced pressure and dried under reduced pressure at 50° C. to give the title composition.

$^1$H NMR ($CDCl_3$) δ: 0.85-0.88 (12H, m), 1.22-1.57 (82H, m), 1.85-1.91 (4H, m), 3.09 (2H, t), 3.38 (4H, t), 4.27 (2H, t), 7.56-7.60 (2H, m), 7.62-7.70 (1H, m);

$^{19}$F NMR ($CDCl_3$) δ: −133.9 (8F,s), −163.7 (4F,t), −167.7 (8F, m).

It was confirmed that the composition obtained in Example 9 dissolves in n-hexane at a concentration of 10 wt %.

Example 10

Composition Containing 2-nonadecyl-1-octadecylimidazolium tetrakis(pentafluorophenyl)borate and tetradecyl ether 2-Nonadecyl-1-octadecylimidazolium tetrakis(pentafluorophenyl)borate (39 mg, 0.03 mmol) obtained in Production Example 11, tetradecyl ether (73.8 mg, 0.15 mmol), and n-hexane (351 mg) were mixed and stirred at 25° C. The mixture became a homogeneous solution. The mixture was concentrated under reduced pressure and dried under reduced pressure at 50° C. to give the title composition.

$^1$H NMR ($CDCl_3$) δ: 0.84-0.90 (36H, m), 1.11-1.83 (302H, m), 2.85-2.89 (2H, m), 3.93 (20H, t), 4.00 (2H, t), 7.10 (1H, d), 7.13 (1H, d);

$^{19}$F NMR ($CDCl_3$) δ: −134.0 (8F,s), −163.6 (4F, t), −167.7 (8F, t).

It was confirmed that the composition obtained in Example 10 dissolves in n-hexane at a concentration of 10 wt %.

Comparative Example 1

N,N-Dioctadecylanilinium tetrakis(pentafluorophenyl)borate

N,N-Dioctadecylaniline (3.3 g, 5.5 mmol) and a lithium tetrakis(pentafluorophenyl)borate tri(diethyl ether) complex (5.0 g, 5.5 mmol) were suspended in n-hexane (50 mL). Then, 1.0 M hydrogen chloride-diethyl ether solution (5.5 mL) was added dropwise, and the mixture was stirred at room temperature for 3 hr. The obtained suspension was filtered, and the filtrate was concentrated under reduced pressure at 50° C. to give the title compound (7.0 g, 90%).

$^1$H NMR ($CDCl_3$) δ: 0.86-0.89 (6H, m), 1.15-1.50 (27H, m) 3.40-3.50 (4H, m), 7.26-7.28 (2H, m), 7.58-7.63 (3H, m);

$^{19}$F NMR ($CDCl_3$) δ: −133.8 (8F, t), −163.3 (4F, t), −167.4 (8F, t).

The compound obtained in Comparative Example 1 was hardly soluble in n-hexane at a concentration of 20 wt %.

Production Example 14

Synthesis of 2-nonadecyl-5-octadecoxypyridine hydrochloride

To a suspension of 2-nonadecyl-5-octadecoxypyridine (1.0 g, 1.6 mmol) obtained in Production Example 6 and n-hexane (100 mL) was added 1 M hydrogen chloride-diethyl ether solution (10 mL) at room temperature, and the mixture was stirred for 1 hr. The solvent in the reaction suspension was evaporated under reduced pressure to give 2-nonadecyl-5-octadecoxypyridine hydrochloride (0.98 g, 93%).

$^1$H NMR ($CDCl_3$) δ: 0.88 (6H, t), 1.24-1.50 (64H, m), 1.78-1.85 (4H, m), 3.13 (2H, t), 4.06 (2H, t), 7.74 (1H, d), 7.74 (1H, dd), 8.21 (1H, d).

Comparative Example 2

2-Nonadecyl-5-octadecoxypyridinium tetrakis(pentafluorophenyl)borate 2-nonadecyl-5-octadecoxypyridine hydrochloride (0.25 g, 0.38 mmol) obtained in Production Example 14 and lithium tetrakis(pentafluorophenyl)borate diethyl ether complex (0.29 g, 0.38 mmol) was suspended in cyclohexane (50 mL), and the mixture was stirred at room temperature for 1 hr. The organic phase was washed with brine, dried over anhydrous magnesium sulfate, and concentrated under reduced pressure. The residue was dried under reduced pressure at 45° C. to give the title compound (0.45 g, 90%).

$^1$H NMR ($CDCl_3$) δ: 0.86-0.90 (6H, m), 1.23-1.43 (64H, m), 1.72-1.86 (4H, m), 2.92 (2H, t), 4.03 (2H, t), 7.64 (1H, d), 7.85 (1H, d), 7.91 (1H, dd);

$^{19}$F NMR ($CDCl_3$) δ: −134.0 (8F, t), −163.4 (4F, t), −167.5 (8F, t).

The compound obtained in Comparative Example 2 was hardly soluble in n-hexane at a concentration of 20 wt %.

Comparative Example 3

N,N-Dinonylanilinium tetrakis(pentafluorophenyl)borate

N,N-Dinonylaniline (0.98 g, 2.8 mmol) and lithium tetrakis(pentafluorophenyl)borate tri(diethyl ether) complex (2.54 g, 2.8 mmol) was suspended in n-hexane (30 mL), a 1.0 M hydrogen chloride-diethyl ether solution (2.8 mL) was added dropwise, and the mixture was stirred at room temperature for 2 hr. The obtained suspension was filtered, and the residue was washed with chloroform. The filtrate was concentrated under reduced pressure at 50° C. to give the title compound (2.19 g, so 76%).

$^1$H NMR ($CDCl_3$) δ: 0.84 (6H, t), 1.14-1.56 (64H, m), 3.43 (4H, br), 7.29 (2H, d), 7.56-7.60 (3H, m);

$^{19}$F NMR ($CDCl_3$) δ: −133.5 (8F, t), −163.4 (4F, t), −167.4 (8F, t)

The compound obtained in Comparative Example 3 was hardly soluble in n-hexane at a concentration of 20 wt %.

Comparative Example 4

Composition Containing N,N-dinonylanilinium tetrakis (pentafluorophenyl)borate and N,N-dinonylaniline To N,N-dinonylanilinium tetrakis(pentafluorophenyl)borate (125 mg, 0.12 mmol) obtained in Comparative Example 3 was added n-hexane (500 mg) to prepare a 20 wt % n-hexane solution. The solution was separated into two layers. To the solution was further added N,N-dinonylaniline (430 mg, 1.25 mmol), and the mixture was stirred and allowed to stand overnight. The solution was separated into two layers. Therefrom it was found that the title composition is hardly soluble in n-hexane at a concentration of 20 wt %.

Comparative Example 51

Composition Containing bis(hydrogenated beef tallow alkyl)methylammonium tetrakis(pentafluorophenyl)borate and bis(hydrogenated beef tallow alkyl)methylamine Bis(Hydrogenated beef tallow alkyl)methylammonium tetrakis(pentafluorophenyl)borate (used as [Comparative Example 6] in the following Experimental Example) (133.2 mg) obtained by a method known per se (Japanese Patent Publication No. 2000-507157), bis(hydrogenated beef tallow alkyl)methylamine (Armeen M2HT (registered trade mark)) (11.2 mg), and n-hexane (533 mg) were mixed and stirred at room temperature. The mixture became a homogeneous solution. The mixture was concentrated under reduced pressure and dried under reduced pressure at 50° C. to give the title compound.

$^{19}$F NMR ($CDCl_3$) δ: −134.1 (8F, d), −163.0 (4F, t), −167.3 (8F, t).

[Experimental Example] (Evaluation of Polymerization Performance)

A general polymerization method using the compound or composition of the present invention as a cocatalyst is shown below.

Into 100 mL autoclave in a glove box were added 1-octene, triisobutylaluminum (TIBA, 0.55 M n-hexane solution) and a solvent (methylcyclohexane (MCH)) to give a comonomer solution. A polymerization catalyst (dimethylsilylene(tert-butylamide)-(tetramethylcyclopentadienyl)-titanium (IV)-dichloride (CGC)), triisobutylaluminum (0.55 M n-hexane solution), and a solvent were added to prepare a catalyst solution at a predetermined concentration, and the solution was transferred to a Schlenk flask. The cocatalyst was dissolved in a solvent, and a cocatalyst solution at a predetermined concentration was prepared and transferred to the Schlenk flask. The comonomer solution, the catalyst solution, and the cocatalyst solution were mixed, and adjusted such that the total amount of the solvent and the total amount of triisobutylaluminum would be constant at the time of the reaction. The inside of the autoclave was purged with ethylene gas, the catalyst solution and the cocatalyst solution were successively added to the autoclave, and the ethylene pressure was immediately adjusted to a predetermined pressure, and the mixture was stirred at a predetermined temperature (25° C.) for a predetermined time. The reaction mixture was ice-cooled, the ethylene gas was removed, the mixture was poured into methanol (100 mL) containing hydrochloric acid (3 mL), and the mixture was stirred at room temperature for 30 min. The precipitate was collected by filtration and dried under reduced pressure at 60° C. to give an ethylene-octene copolymer.

(Measurement of Melting Point)

Measurement by the differential scanning calorimetry method (DSC) was performed using DSC6220 instrument (Seiko Instruments Inc.). A sample (polymer) was heated at a rate of 10° C./min from 40° C. to 150° C., and the melting point was measured.

The results of the polymerization reaction at 25° C. using various cocatalysts are respectively shown in Table 1.

TABLE 1

| cocatalyst | catalyst amount (μmol) | time (min) | yield (g) | activity (kg/mol of Ti · h) | melting point (° C.) |
|---|---|---|---|---|---|
| Comparative Example 6[1)] | 0.1 | 6 | 0.033 | 3300 | 77.6 |
| Comparative Example 5 | 0.1 | 6 | 0.030 | 2970 | N.T. |
| Comparative Example 1 | 0.1 | 6 | 0.060 | 6000 | 78.9 |
| Example 1 | 0.1 | 6 | 0.064 | 6400 | 82.3 |
| Example 4 | 0.1 | 6 | 0.12 | 12000 | 74.8 |
| Example 3 | 0.1 | 6 | 0.098 | 9800 | 82.3 |

Reaction conditions; catalyst: CGC, catalyst:cocatalyst = 1:1, TIBA (total amount 3000 μmol), solvent: methylcyclohexane, solvent total amount (40 mL), 1-octene (1 mL), ethylene pressure (8 atm), 25° C.

[1)]Bis(hydrogenated beef tallow alkyl)methylammonium tetrakis(pentafluorophenyl)borate According to Table 1, it was confirmed that Example 1, 3, and 4 show polymerization activity equal to or higher than that of Comparative Example 1, 5 or 6.

INDUSTRIAL APPLICABILITY

The composition of the present invention is soluble (or easily soluble) in hydrocarbon solvents, particularly aliphatic hydrocarbon solvents, and does not become a catalyst poison. Thus, it is useful as a cocatalyst for polymerization of olefins and dienes.

This application is based on patent application Nos. 2020-043246 filed in Japan (filing date: Mar. 12, 2020) and 2020-209070 filed in Japan (filing date: Dec. 17, 2020), the contents of which are incorporated in full herein.

The invention claimed is:

1. A composition comprising:

(I) base A or a compound having a total carbon number of not less than 8 and represented by formula (5):

(5)

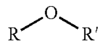

wherein R and R' are each independently an optionally substituted $C_{1-30}$ alkyl group, an optionally substituted $C_{3-15}$ cycloalkyl group, or an optionally substituted $C_{6-14}$ aryl group; and (II) a compound represented by formula (1):

(1)

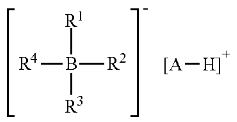

wherein $R^1$, $R^2$, $R^3$ and $R^4$ are each independently a $C_{6-14}$ aryl group substituted by one or more fluorine atoms or fluoro $C_{1-4}$ alkyl groups; and $[A-H]^+$ is a base A-derived cation;

wherein the base A is:

a 5 or 6-membered monocyclic nitrogen-containing aromatic heterocyclic compound having a total carbon number of not less than 25 and substituted by the same or different, two or more $C_{9-30}$ alkyl groups or $C_{9-30}$ alkoxy groups (6)

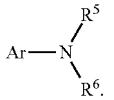

2. The composition according to claim 1, wherein (I) is base A.

3. The composition according to claim 1, wherein (I) is a compound represented by the formula (5).

4. The composition according to claim 1, wherein $R^1$, $R^2$, $R^3$ and $R^4$ are each independently a phenyl group, a 1-naphtyl group, a 2-naphthyl group, a 2-biphenylyl group, a 3-biphenylyl group, a 4-biphenylyl group, a 1-anthryl group, a 2-anthryl group, a 9-anthryl group, a 9-phenanthryl group, or a 3-phenanthryl group, each of which is substituted by one or more fluorine atoms or trifluoromethyl groups.

5. The composition according to claim 1, wherein all of $R^1$, $R^2$, $R^3$ and $R^4$ are pentafluorophenyl groups, 2,2',3,3',4',5,5',6,6'-nonafluoro-4-(1,1'-biphenylyl) groups, 2,3,4,5,6,7,8-heptafluoro-1-naphthyl groups, or 1,3,4,5,6,7,8-heptafluoro-2-naphthyl groups.

6. The composition according to claim 2, wherein the base A is a 5- or 6-membered monocyclic nitrogen-containing aromatic heterocyclic compound having a total carbon number of not less than 25 and substituted by the same or different two $C_{9-30}$ alkyl groups or $C_{9-30}$ alkoxy groups.

7. The composition according to claim 6, wherein the 5- or 6-membered monocyclic nitrogen-containing aromatic heterocyclic compound is pyridine or imidazole.

8. The composition according to claim 2, wherein a content of the base A with respect to 1 mol of the compound represented by the formula (1) is within a range of 0.01 to 10 mol.

9. The composition according to claim 3, wherein the R and R' are each independently a $C_{1-30}$ alkyl group, and a total carbon number of the R and R' is not less than 8.

10. The composition according to claim 3, wherein the R and R' are each independently a $C_{1-30}$ alkyl group, and a total carbon number of the R and R' is not less than 16.

11. The composition according to claim 3, wherein a content of the compound represented by the formula (5) with respect to 1 mol of the compound represented by the formula (1) is within a range of 0.1-10 mol.

12. A cocatalyst for polymerization of at least one kind of monomer selected from the group consisting of an olefin and a diene, comprising the composition of claim 1.

13. A method for producing the composition according to claim 1, comprising reacting a compound represented by formula (3):

(3)

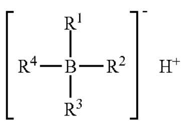

wherein $R^1$, $R^2$, $R^3$ and $R^4$ are each independently a $C_{6-14}$ aryl group substituted by one or more fluorine atoms or fluoro $C_{1-4}$ alkyl groups; and the base A;

wherein the base A is present in an amount exceeding 1 mol per 1 mol of the compound represented by the formula (3).

14. The method according to claim 13, wherein the amount of the base A is within a range of 1.01 to 3 mol with respect to 1 mol of the compound represented by the formula (3).

15. A method for producing the composition according to claim 1, comprising reacting a compound represented by formula (4):

(4)

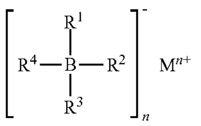

wherein $R^1$, $R^2$, $R^3$ and $R^4$ are each independently a $C_{6-14}$ aryl group substituted by one or more fluorine atoms or fluoro $C_{14}$ alkyl groups; and M is an alkali metal or an alkaline earth metal; and n is 1 or 2;

the base A; and protonic acid, wherein the base A is present in an amount exceeding 1 mol per 1 mol of the compound represented by the formula (4).

16. A method for producing the composition according to claim 1, comprising reacting a compound represented by formula (4):

(4)

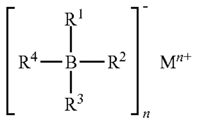

wherein $R^1$, $R^2$, $R^3$ and $R^4$ are each independently a $C_{6-14}$ aryl group substituted by one or more fluorine atoms or fluoro $C_{1-4}$ alkyl groups; and M is an alkali metal or an alkaline earth metal; and n is 1 or 2; and 1 mol of the base A per 1 mol of the compound represented by the formula (4) and protonic acid; and thereafter, adding not less than 0.1 mol of a compound having a total carbon number of not less than 8 and represented by formula (5):

(5)

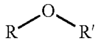

wherein R and R' are each independently an optionally substituted $C_{1-30}$ alkyl group, an optionally substituted $C_{3-15}$ cycloalkyl group, or an optionally substituted $C_{6-14}$ aryl group, per 1 mol of the compound represented by the formula (4).

17. A method for producing a polymer, comprising polymerizing at least one kind of monomer selected from the group consisting of olefins and dienes with the composition according to claim 1 as a cocatalyst.

18. The composition according to claim 1, wherein the base A is pyridine having a total carbon number of not less than 35 and substituted by one $C_{14-30}$ alkyl group and one $C_{14-30}$ alkoxy group.

* * * * *